United States Patent
Barman et al.

(10) Patent No.: US 12,201,668 B2
(45) Date of Patent: Jan. 21, 2025

(54) ADIPONECTIN PEPTIDOMIMETICS FORMULATIONS

(71) Applicant: ALLYSTA PHARMACEUTICALS, INC., San Mateo, CA (US)

(72) Inventors: Shikha P Barman, Bedford, MA (US); Kevin L Ward, Arlington, MA (US); Yugang Chen, Winchester, MA (US)

(73) Assignee: Allysta Pharmaceuticals, Inc., Bellevue, WA (US)

( * ) Notice: Subject to any disclaimer, the term of this patent is extended or adjusted under 35 U.S.C. 154(b) by 0 days.

(21) Appl. No.: 16/662,932

(22) Filed: Oct. 24, 2019

(65) Prior Publication Data

US 2020/0129585 A1    Apr. 30, 2020

Related U.S. Application Data

(60) Provisional application No. 62/749,861, filed on Oct. 24, 2018.

(51) Int. Cl.
*A61K 38/10* (2006.01)
*A61K 47/10* (2017.01)
*A61P 27/02* (2006.01)

(52) U.S. Cl.
CPC .............. *A61K 38/10* (2013.01); *A61K 47/10* (2013.01); *A61P 27/02* (2018.01)

(58) Field of Classification Search
None
See application file for complete search history.

(56) References Cited

U.S. PATENT DOCUMENTS

| 10,537,608 | B2 * | 1/2020 | Hsu | ................. | C07K 14/5759 |
| 2008/0268051 | A1 | 10/2008 | Hughes et al. | | |
| 2013/0295042 | A1 | 11/2013 | Anantharamaiah et al. | | |
| 2014/0037712 | A1 * | 2/2014 | Yoon | ................. | A61K 9/0048 |
| | | | | | 514/9.7 |
| 2014/0057833 | A1 * | 2/2014 | Otvos | ................. | C07K 7/06 |
| | | | | | 514/1.9 |
| 2016/0101145 | A1 * | 4/2016 | Annis | ................. | A61K 9/0019 |
| | | | | | 514/21.1 |
| 2018/0078531 | A1 * | 3/2018 | Bingaman | .............. | A61K 47/32 |
| 2018/0078616 | A1 | 3/2018 | Hsu | | |

FOREIGN PATENT DOCUMENTS

| WO | WO 93/21903 | * 11/1993 |
| WO | 2012142142 A2 | 10/2012 |
| WO | 2016049355 A1 | 3/2016 |
| WO | 2016179007 A1 | 11/2016 |
| WO | WO 2016/179007 | * 11/2016 |

OTHER PUBLICATIONS

Costello et al., Pancreat Disord Ther; Suppl 4; doi: 10.4172/2165-7092.S4-002 (Year: 2013).*
Hersh et al., Clinical Infectious Diseases 2012;54(11):1677-8 (Year: 2012).*
Mullin, Ebola outbreak rages on as drug development remains slow, Fierce Biotech, 2014 (Year: 2014).*
Prion Alliance, What are the potential treatments for prion disease?, Feb. 4, 2014 (Year: 2014).*
International Search Report on PCT/US19/57876, mailed on Jan. 16, 2020.
Supplementary European Search Report on EP19876498, mailed on Nov. 21, 2022.

* cited by examiner

*Primary Examiner* — Sergio Coffa
(74) *Attorney, Agent, or Firm* — Yong Chen; Lin Sun-Hoffman; Liu Chen & Hoffman LLI

(57) ABSTRACT

Disclosed are compositions and methods for the use of adiponectin peptidomimetics in therapeutic applications. The compositions can include a peptide, for example, D-Asn-Ile-Pro-Nva-Leu-Tyr-D-Ser-Phe-Ala-D-Ser-NH$_2$, a solubilizer, a surfactant(s), a buffer, optionally boric acid and optionally mannitol. The osmolality of the composition can be between 260 to 330 mOsm/kg and the pH can be between 4.5 to 5.5. Methods of using the compositions in treating certain eye disease(s) are also disclosed.

9 Claims, 4 Drawing Sheets

Specification includes a Sequence Listing.

ADIPONECTIN PEPTIDOMIMETICS FORMULATIONS

CROSS REFERENCE TO RELATED APPLICATION

This application claims priority to U.S. Provisional Application No. 62/749,861, filed on Oct. 24, 2018, the disclosure of which is incorporated by reference herein in its entirety.

BACKGROUND

Disclosed are compositions for treating ocular disorders. More specifically, disclosed are compositions and methods for the use of adiponectin peptidomimetics in therapeutic applications.

There are few effective therapeutic options for the majority of patients with dry eye and ocular diseases associated with inflammation. Accordingly, there is a high unmet need for effective and safe therapies. Adiponectin is a protein predominately secreted by adipose tissue and is associated with inflammatory responses. Adiponectin exerts an immunoregulatory effect by increasing levels of anti-inflammatory cytokines IL-10 and IL-1RA and decreasing levels of pro-inflammatory proteins IL-6, TNF-$\alpha$, and IFN-$\gamma$. Topical application of adiponectin in experimental models of dry eye decreases inflammation in the ocular surface and lacrimal gland. Low molecular weight (1 to 2 kDa) peptide compounds that mimic the activity or function of adiponectin protein are useful as therapies in treating patients with dry eye and ocular diseases associated with inflammation.

However, low molecular weight adiponectin peptidomimetics are susceptible to degradation by fragmentation, deamidation, oxidation and hydrolysis. Thus, the challenges in developing a formulation strategy for these small peptides requires a balance of physiochemical variables that would allow chemical stabilization into a peptide drug product that allows normal use at room temperature conditions and storage long-term under refrigerated conditions, solubilization into therapeutically relevant peptide concentrations, ensuring that the resultant solution is non-irritating and ensuring that aggregation of peptide due to loss/fragmentation of hydrophilic sequences is prevented.

Formulating adiponectin peptidomimetics have three primary objectives: (a) prevent aggregation, (b) minimize degradation and (c) minimize irritation. The aggregation behavior of the peptides are due to their high hydrophobicity. At higher pH, deamidation of peptide can occur, which results in conversion of the gross positively-charged peptide to a neutral peptide. Due to the hydrophobic nature of other amino acid residues on this peptide, the lack of charge leads to micro-collapse of the peptide chains and resultant precipitation. The formulations of the present invention address these challenges.

SUMMARY OF THE INVENTION

An aspect of this invention is a composition comprising: a therapeutically effective amount of a 1 kDa to 2 kDa peptide, a generally recognized as safe solubilizer, one or more generally recognized as sate surfactants and a generally recognized as safe buffer, optionally boric acid and optionally mannitol; wherein the osmolality is between 260 to 330 mOsm/kg and the pH is between 4.5 to 5.5. When boric acid and mannitol are included, boric acid can be generally from 0.05% to 1.0%, or from 0.05% to 0.2%, of the total composition, and mannitol can be generally from 0.5% to 5.0%, or from 2.0% to 4.0% of the total composition.

An aspect of this invention is a composition comprising: a therapeutically effective amount a 1 kDa to 2 kDa adiponectin peptidomimetic, a generally recognized as sate solubilizer, one or more a generally recognized as safe surfactants a generally recognized as safe buffer, optionally boric acid and optionally mannitol; wherein the osmolality of is between 260 to 330 mOsm/kg and the pH is between 4.5 to 5.5.

An aspect of this invention is a method for treating a disease in a patient by administering to the patient a composition comprising: a therapeutically effective amount of a 1 kDa to 2 kDa peptide, a generally recognized as safe solubilizer, one or more generally recognized as safe surfactants, a generally recognized as safe buffer, optionally boric acid and optionally mannitol; wherein the osmolality is between 260 to 330 mOsm/kg and the pH is between 4.5 to 5.5.

An aspect of this invention is a method for treating a disease in a patient by administering to the patient a composition comprising: a therapeutically effective amount a 1 kDa to 2 kDa adiponectin peptidomimetic, a generally recognized as safe solubilizer, one or more a generally recognized as safe surfactants, a generally recognized as safe buffer, optionally boric acid and optionally mannitol; wherein the osmolality is between 260 to 330 mOsm/kg and the pH is between 4.5 to 5.5.

DETAILED DESCRIPTION OF THE INVENTION

Definitions

Figure 1:
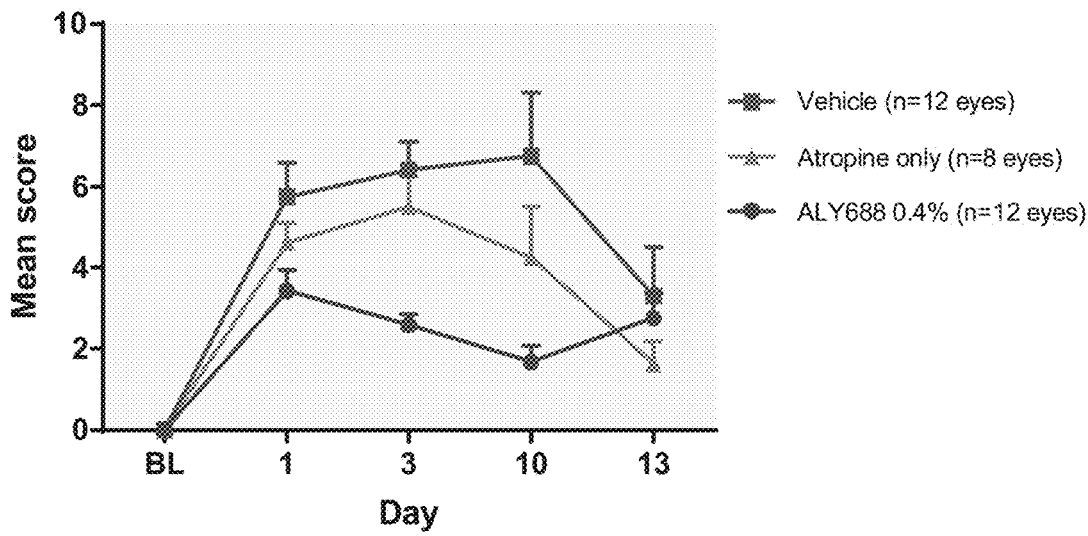
FIG. 1 shows corneal staining results of the use of a formulation of the present invention in the eyes of test rabbits.

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise.

The term "dry eye" refers to a multifactorial disease of the tears and ocular surface (including the cornea, conjunctiva, and eye lids) results in symptoms of discomfort, visual disturbance and tear film instability with potential damage to the ocular surface, as defined by the "The Definition and Classification of Dry Eye Disease: Guidelines from the 2007 International Dry Eye Work Shop," Ocul Surf, 2007, 5(2): 75-92). Dry eye can be accompanied by increased osmolarity of the tear film and inflammation of the ocular surface. Dry eye includes dry eye syndrome, keratoconjunctivitis sicca (KCS), dysfunctional tear syndrome, lacrimal keratoconjunctivitis, evaporative tear deficiency, aqueous tear deficiency, and LASIK-induced neurotrophic epitheliopathy (LE).

The term "ocular disease associated with inflammation" refers to a disease or disorder of the eye wherein inflammation causes damage to the ocular surface system. As used herein, "the ocular surface system" includes the cornea, conjunctiva, lacrimal glands, meibomian glands, nasolacrimal duct, and their associated tear and connective tissue matrices, as well as the eyelids and eyelashes, all integrated by continuous epithelia and interconnected nervous, endocrine, immune, and vascular systems.

The term "a symptom" refers to a subjective indication or observation of a disorder or disease experienced or perceived by a patient.

The term "a clinical sign" refers to an objective indication, observation or evidence of a disorder or a disease that may be detected or interpreted by a clinician.

The term "adiponectin" refers to a polypeptide that is primarily derived from adipocytes. The adiponectin polypeptide is composed of 244 amino acid residues containing a short non-collagenous N-terminal segment (about 130 amino acids) followed by a collagen like sequence (Maeda et al., BBRC, 1996, 221: 286-289). The amino acid sequence of human adiponectin polypeptide is found, for example, in NCBI Ref. Sequence No. NP 004788.1 or UniPro Ref. No. Q15848. Adiponectin can form a homotrimer that is similar in size and overall structure to complement protein C1q, with particularly high homology (about 65-70% homology) to C1q in the C-terminal globular domain. This globular domain (about 130 amino acids) is believed to be essential for the biological activity of natural (native) adiponectin. The crystal structure of adiponectin revealed additional high structural similarity between this same globular domain and TNFa (about 60% homology).

The term "an adiponectin peptidomimetic" refers to an oligo-polyamide compound, consisting of natural or/and non-natural amino acid residues, that mimics the activity or function of adiponectin protein. An adiponectin peptidomimetic may have the ability to bind to or interact with one or more adiponectin receptors (AdipoR1 and AdipoR2) or variants thereof. A peptidomimetic may be a backbone modified peptide, any polyamide or other polymeric structure resembling peptides, peptides containing non-natural amino acid residues or a peptide derivative.

The term "peptide" refers to an organic compound comprising a chain of two or more amino acids covalently joined by peptide bonds. Peptides may be referred to with respect to the number of constituent amino acids, i.e., a dipeptide contains two amino acid residues, a tripeptide contains three, etc.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) The Peptides, 5: 342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, N-methyl-arginine, norleucine, N-methylaminobutyric acid, naphthyl alanine, phenylglycine, beta-phenylproline, tert-leucine, 4-aminocyclohexylalanine, N-methyl-norleucine, norvaline, 3,4-dehydroproline, N,N-dimethylaminoglycine, N-methylaminodycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "side chain" means groups that are attached to the peptide backbone, and typically refers to the group attached to the a-carbon of an .alpha.-amino acid. For example, for the side chains of the proteinogenic amino acids include: methyl (alanine), hydroxymethyl, benzyl (phenylalanine), mercaptomethyl (cysteine and carboxymethyl (aspartic acid).

The term "non-natural amino acid" is used to refer to an amino acid which does not exist on its own in nature, but rather, has been synthesized or created by man. Examples of non-natural amino acids include iodinated tyrosine, methylated tyrosine, glycosylated serine, glycosylated threonine, azetidine-2-carboxylic acid, 3,4-dehydroproline, perthiaproline, canavanine, ethionine, norleucine, selenomethionine, animohexanoic acid, telluromethionine, homoallylglycine, and homopropargyiglycine. D-amino acids are also examples of non-natural amino acids.

"Nva" corresponds to the non-natural amino acid norvaline, also known as 2(L)-aminopentanoic acid. "NvaNH2" corresponds to 2(L)-aminopentanamide. "Aca" corresponds to the non-natural amino acid 6-aminocaproic acid, also known as 6-amino-hexanoic acid. "AcpNH2" corresponds to 6-aminocapramide, also known as 6-amino-hexanamide. "Dap(Ac)" corresponds to N2(3)-acetyl-diaminopropionic acid. "Dbu" corresponds to 2,4-diaminobutyric acid. "Glc" corresponds to glucose. "betaGlc" corresponds to beta-glucose. "Serbeta(Glc)" corresponds to serine glycosylated with a beta-glucosyl residue on the alcohol hydroxyl group. "Thr(GalNAc)" corresponds to threonine glycosylated with an N-acetyl galactosaminyl residue on the alcohol hydroxyl group. "Tyr(I2)" corresponds to 3,5-diiodotyrosine. "N-MeArg" corresponds to N-methyl-arginine. "betaAla" corresponds to beta-alanine, also known as 3-aminopropanoic acid. "betaAla-NH2" corresponds to the amide derivative of beta-alanine, also known as 3-aminopropanamide. "(D)-Ser" corresponds to D-serine. "Apa" corresponds to aminopentanoic acid. "AlloThr" corresponds to allo-threonine, also known as (2S,3 S)-2-amino-3-hydroxybutanoic acid. "3Hyp" corresponds to 3-hydroxyproline. "4Hyp" corresponds to 4-hydroxyproline.

As used herein, the term "hydroxylated acyclic amino acid" refers to an acyclic amino acid that contains at least one alcohol hydroxyl group in its structure. Preferred, but non-limiting, examples of hydroxylated acyclic amino acid are serine. (D)-serine, threonine, (D)-threonine, (L)-alto-threonine, (D)-alto-threonine, (L)-isoserine, (D)-isoserine, (D)-β-homoserine, (L)-homoserine, and (D)-homoserine.

The term "peptide transduction domain" is used to indicate a peptide, or derivative thereof, that is capable of crossing cell membranes and of directing the transport of a peptide, protein, or molecule associated with the protein transduction domain, from the outside of a cell into the cytoplasm of the cell through the cytoplasmic membrane of the cell.

The term "conjugated" referring to the linking of two peptides means that the two peptides are covalently linked to one another. The linking may be accomplished directly, through the formation of an amide bond between the carboxyl group of one peptide and an amino group of the other peptide, or by means of a linking group wherein the linking group has covalent bonds to each of the peptides. For example, the linking group may be a peptide chain, an amino acid, or any group having at least two functional groups and capable of forming covalent bond to each of the two peptide chains.

"Generally recognized as safe" (GRAS) is an American Food and Drug Administration (FDA) designation that a chemical or substance added to food is considered safe by experts, and so is exempted from the usual Federal Food, Drug, and Cosmetic Act (FFDCA) food additive tolerance requirements.

The term "therapeutically effective amount," "effective amount" or "therapeutically effective dose" refers to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. In the context of the present invention, the effective amount of an adiponectin peptidomimetic compound can vary depending on co-administration of other therapeutics or disease profile of the individual (among other factors such as age, severity of disease, etc.).

The terms "therapy," "treatment," and "amelioration" refer to any reduction in the severity of symptoms. In the case of treating an ocular disorder, e.g., dry eye, the terms can refer to adding artificial tears, conserving tears, reducing tear evaporation, increasing tear production, reducing inflammation of the eyelids or eye surface, reducing ocular signs to dry eye, etc. As used herein, the terms "treat" and "prevent" are not intended to be absolute terms. Treatment can refer to any delay in onset, amelioration of symptoms, improvement in patient's quality of life, etc. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The term "treating" or "treatment" refers to the treating or treatment of a disease or medical condition (such as dry eye or an ocular disease associated with inflammation) in a patient, such as a mammal (particularly a human or an animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating one or more symptoms of the disease or medical condition in a patient. The term encompasses the prophylactic treatment of a disease or condition as to prevent or reduce the risk of acquiring or developing a specific disease or condition, or to prevent or reduce the risk of recurrence.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (h) the limitations inherent in the art of compounding such active compound(s).

The term "subject," "individual" or "patient" typically includes humans, but can also include other animals such as, e.g., other primates, rodents, canines, felines, equines, ovines, porcines, and the like.

Preferred Embodiments of the Invention

A preferred is a composition comprising an adiponectin peptidomimetic, a generally recognized as safe solubilizer selected from polypropylene glycol, glycerol, PEG400 and propylene glycol, a generally recognized as safe surfactant selected from Tween 80, Tyloxapol, Poloxamer, PEG 40 Hydrogenated Caster Oil, PEG 35 Caster Oil and PEG 40 Sterate and an acetate buffer; wherein the osmolality is between 260 to 330 mOsm/kg and the pH is between 4.5 to 5.5.

As used herein, all percentages for components of all formulations refer to weight percentages. Preferred is a formulation comprising 0.01% to 2% D-Asn-Ile-Pro-Nva-Leu-Tyr-D-Ser-Phe-Ala-D-Ser-NH$_2$ (SEQ ID NO:1), 1% to 2% propylene glycol, 0.08% to 0.12% Tyloxapol or Poloxamer, 0.02% to 0.20% acetic acid and 0.05% to 0.5% sodium acetate; wherein osmolality is between 260 to 330 mOsm/kg and the pH is between 4.5 to 5.5.

Preferred is a formulation comprising: 0.02% to 1.0% D-Asn-lie-Pro-Nva-Leu-Tyr-D-Ser-Phe-Ala-D-Ser-NH$_2$, 1.20% to 1.90% propylene glycol, 0.10% Tyloxapol or Poloxamer, 0.04% to 0.20% acetic acid and 0.08% to 0.42% sodium acetate; wherein osmolality is between 260 to 330 mOsm/kg and the pH is between 4.5 to 5.5.

Preferred is a composition comprising: 1.0% D-Asn-Ile-Pro-Nva-Leu-Tyr-D-Ser-Phe-Ala-D-Ser-NH$_2$, 1.77% propylene glycol, 0.10% Tyloxapol, 0.14% acetic acid and 0.08% sodium acetate; wherein osmolality is between 260 to 330 mOsm/kg and the pH is between 4.5 to 5.5.

Preferred is a composition comprising: 0.5% D-Asn-Ile-Pro-Nva-Leu-Tyr-D-Ser-Phe-Ala-D-Ser-NH$_2$, 1.58% propylene glycol, 0.10% Tyloxapol, 0.09% acetic acid and 0.24% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.57% propylene glycol, 0.10% Tyloxapol, 0.09% acetic acid and 0.24% sodium acetate; wherein is between 260 to 330 mOsm/kg and the pH is between 4.5 to 5.5.

Preferred is a composition comprising: 0.5% D-Asn-Ile-Pro-Nva-Leu-Tyr-D-Ser-Phe-Ala-D-Ser-NH$_2$, 1.43% propylene glycol, 0.10% Tyloxapol, 0.04% acetic acid and 0.34% sodium acetate; wherein osmolality is between 260 to 330 mOsm/kg and the pH is between 4.5 to 5.5.

Preferred is a composition comprising: 0.5% D-Asn-Ile-Pro-Nva-Leu-Tyr-D-Ser-Phe-Ala-D-Ser-NH$_2$, 1.44% propylene glycol, 0.10% Tyloxapol, 0.04% acetic acid and 0.34% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.72% propylene glycol, 0.10% Poloxamer 188, 0.11% acetic acid and 0.09% sodium acetate; wherein osmolality is between 260 to 330 mOsm/kg and the pH is between 4.5 to 5.5.

Preferred is a composition comprising: 0.50% D-Asn-Ile-Pro-Nva-Leu-Tyr-D-Ser-Phe-Ala-D-Ser-NH$_2$, 1.73% propylene glycol, 0.10% Poloxamer 188, 0.11% acetic acid and 0.09% sodium acetate; wherein osmolality is between 260 to 330 mOsm/kg and the pH is between 4.5 to 5.5.

Preferred is a composition comprising: 0.25% D-Asn-Ile-Pro-Nva-Leu-Tyr-D-Ser-Phe-Ala-D-Ser-NH$_2$, 1.74% propylene glycol, 0.10% Poloxamer 188, 0.11% acetic acid and 0.09% sodium acetate; wherein osmolality is between 260 to 330 mOsm/kg and the pH is between 4.5 to 5.5.

Preferred is a composition comprising: 0.50% D-Asn-Ile-Pro-Nva-Leu-Tyr-D-Ser-Phe-Ala-D-Ser-NH$_2$, 1.55% propylene glycol, 0.10% Poloxamer 188, 0.10% acetic acid and 0.24% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.55% propylene glycol, 0.10% Poloxamer 188, 0.10% acetic acid and 0.24% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.40% propylene glycol, 0.20% Poloxamer 188, 0.19% acetic acid and 0.30% sodium acetate; wherein osmolality is between 260 to 330 mOsmikg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.38% propylene glycol, 0.10% Tyloxapol, 0.19% acetic acid and 0.30% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.25% propylene glycol, 0.10% Tyloxapol, 0.17% acetic acid and 0.41% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.54% propylene glycol, 0.10% Tyloxapol, 0.19% acetic acid and 0.14% sodium acetate; wherein osmolality is between 260 to 330 mOsm/kg and the pH is between 4.5 to 5.5.

Preferred is a composition comprising: 0.80% D-Asn-Ile-Pro-Nva-Leu-Tyr-D-Ser-Phe-Ala-D-Ser-NH$_2$, 1.54% propylene glycol, 0.10% Tyloxapol, 0.19% acetic acid and 0.14% sodium acetate; wherein osmolality is between 260 to 330 mOsm/kg and the pH is between 4.5 to 5.5.

Preferred is a composition comprising: 0.50% D-Asn-Ile-Pro-Nva-Leu-Tyr-D-Ser-Phe-Ala-D-Ser-NH$_2$, 1.55% propylene glycol, 0.10% Tyloxapol, 0.19% acetic acid and 0.14% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.53% propylene glycol, 0.10% Tyloxapol, 0.19% acetic acid and 0.14% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.86% propylene glycol, 0.10% Tyloxapol, 0.13% acetic acid and 0.10% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.67% propylene glycol, 0.10% Tyloxapol, 0.15% acetic acid and 0.11% sodium acetate; wherein osmolality is between 260 to 330 mOsm/kg and the pH is between 4.5 to 5.5.

Preferred is a composition comprising: 1.00% D-Asn-Ile-Pro-Nva-Leu-Tyr-D-Ser-Phe-Ala-D-Ser-NH$_2$, 1.62% propylene glycol, 0.10% Tyloxapol, 0.17% acetic acid and 0.13% sodium acetate; wherein osmolality is between 260 to 330 mOsm/kg and the pH is between 4.5 to 5.5.

Preferred is a formulation comprising: 0.5% to 1% D-Asn-Ile-Pro-Nva-Leu-Tyr-D-Ser-Phe-Ala-D-Ser-NH$_2$, 1.43% to 1.55% propylene glycol, 0.10% Poloxamer 188, 0.04% to 0.10% acetic acid and 0.24% to 0.34% sodium acetate; wherein osmolality is between 260 to 330 mOsm/kg and the pH is between 4.5 to 5.5.

Preferred is a formulation comprising: 1.00% D-Asn-Ile-Pro-Nva-Leu-Tyr-D-Ser-Phe-Ala-D-Ser-NH$_2$, 1.55% propylene glycol, 0.10% Poloxamer 188, 0.10% acetic acid, 0.24% sodium acetate; wherein osmolality is between 260 to 330 mOsm/kg and the pH is between 4.5 to 5.5.

Preferred is a formulation comprising: 0.5% D-Asn-Ile-Pro-Nva-Leu-Tyr-D-Ser-Phe-Ala-D-Ser-NH$_2$, 1.43% propylene glycol, 0.10% Poloxamer 188, 0.04% acetic acid, 0.24; wherein osmolality is is between 260 to 330 mOsm/kg and the pH is between 4.5 to 5.5.

Preferred is a formulation comprising: 0.4% to 1.00% D-Asn-Ile-Pro-Nva-Leu-Tyr-D-Ser-Phe-Ala-D-Ser-NR$_2$, 0.193% to 0.20% propylene glycol, 0.09 to 0.10% Tyloxapol, 0.014% to 0.07% acetic acid, 0.06% to 0.138% sodium acetate, 0.09% boric acid, and 3.127% to 3.66% mannitol.

Preferred is a formulation comprising: 0.401% D-Asn-Ile-Pro-Nva-Leu-Tyr-D-Ser-Phe-Ala-D-Ser-NH$_2$, 0.193% propylene glycol, 0.097% Tyloxapol, 0.014% acetic acid, 0.138% sodium acetate, 0.09% boric acid, and 3.65% mannitol.

Preferred is a formulation comprising: 1.00% D-Asn-Ile-Pro-Nva-Leu-Tyr-D-Ser-Phe-Ala-D-Ser-NH$_2$, 0.20% propylene glycol, 0.10% Tyloxapol, 0.07% acetic acid, 0.06% sodium acetate, 0.09% boric acid, and 3.66% mannitol.

Preferred is a method for treating a disease in a patient by administering to the patient a formulation comprising: an adiponectin peptidomimetic, a generally recognized as safe solubilizer selected from polypropylene glycol, glycerol, PEG400 and propylene glycol, a generally recognized as safe surfactant selected from Tween 80, Tyloxapol, Poloxamer, PEG 40 Hydrogenated Caster Oil, PEG 35 Caster Oil and PEG 40 Sterate, and an acetate buffer; wherein the osmolality is between 260 to 330 mOsm/kg and the pH is between 4.5 to 5.5.

Preferred is a method for treating a disease in a patient by administering to the patient a formulation comprising: 0.1% to 2% D-Asn-Ile-Pro-Nva-Leu-Tyr-D-Ser-Phe-Ala-D-Ser-NH$_2$, 1% to 2% propylene glycol, 0.08% to 0.12% Tyloxapol or Poloxamer, 0.02% to 0.20% acetic acid and 0.05% to 0.5% sodium acetate; wherein osmolality is between 260 to 330 mOsm/kg and the pH is between 4.5 to 5.5.

Preferred is a method for treating a disease in a patient by administering to the patient a formulation comprising: 0.20% to 1.0% D-Asn-Ile-Pro-Nva-Leu-Tyr-D-Ser-Phe-Ala-D-Ser-NH$_2$, 1.20% to 1.90% propylene glycol, 0.10% Tyloxapol or Poloxamer, 0.04% to 0.20% acetic acid and 0.08% to 0.42% sodium acetate; wherein osmolality is between 260 to 330 mOsm/kg and the pH is between 4.5 to 5.5.

Preferred is a method for treating an ocular disease associated with inflammation disease in a patient by administering to the patient a formulation comprising: 0.20% to 1.0% D-Asn-Ile-Pro-Nva-Leu-Tyr-D-Ser-Phe-Ala-D-Ser-NH$_2$, 1.20% to 1.90% propylene glycol., 0.10% Tyloxapol or Poloxamer, 0.04% to 0.20% acetic acid and 0.08% to 0.42% sodium acetate; wherein osmolality is between 260 to 330 mOsm/kg and the pH is between 4.5 to 5.5.

Preparations of Compounds of the Formulation of the Invention

Peptidomimetic compounds of the present invention may be natural peptides, recombinant peptides or synthetic peptides. They may also be chemically synthesized, using, for example, solid phase synthesis methods. Additionally, peptide transduction domains appended to peptides of the invention may be natural or synthetic peptides, and may be either prepared by isolation from natural sources or may be synthesized.

The peptides of the present invention may be synthesized de novo using peptide synthesis methods. In such methods, the peptide chain is prepared by a series of coupling reactions in Which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldiimidazole; various active esters, e.g., esters of N-hydroxyphthalimide or N-hydroxy-succinimide; and the various cleavage reagents, e.g., trifluoroacetic acid (TEA), HCl in dioxane, boron tris-(trifluoracetate) and cyanogen bromide; and reaction in solution with isolation and purification of intermediates are methods well-known to those of ordinary skill in the art. The reaction may be carried out with the peptide either in solution or attached to a solid phase support. In the solid phase method, the peptide is released from the solid phase support following completion of the synthesis.

In some embodiments, the peptide synthesis method may follow Merrifield solid-phase procedures. See, e.g., Merrifield, J. Am. Chem. Soc, 1963, 85, 2149-54. Additional information about the solid phase synthetic procedure can be obtained from, for example, Solid Phase Peptide Synthesis: A Practical Approach by E. Atherton and R. C. Sheppard (Oxford University Press, 1989, Solid phase peptide synthesis, by J. M. Stewart and J. D. Young, (2nd edition, Pierce Chemical Company, Rockford, 1984), and the review chapters by R. Merrifield in Advances in Enzymology 32:221-296, edited by F. F. Nold (Interscience Publishers, New York, 1969) and by B. W. Erickson and R. Merrifield in The Proteins Vol. 2, pp. 255 et seq., edited by Neurath and Hill, (Academic Press, New York, 1976). Peptide synthesis may follow synthetic techniques such as those set forth in Fields et al., Introduction to Peptide Synthesis, in Current Protocols in Molecular Biology (Chapter 11, Unit 11.15; John Wiley and Sons, 2008) and Amblard et al. (2006, Molecular Biotechnology, 33:239-254).

The synthesis of peptides by solution methods is described in, for example, The Proteins, Vol. 11, edited by Neurath et al. (3rd Edition, Academic Press 1976). Other general references to the synthesis of peptides include: Peptide Synthesis Protocols, edited by M. W. Pennington and Ben M. Dunn (Humana Press 1994), Principles of Peptide Synthesis, by Miklos Bodanszky (2nd edition, Springer-Verlag, 1993), and Chemical Approaches to the Synthesis of Peptides and Proteins by Paul Lloyd-Williams, F. Albericio, E. Giralt (CRC Press 1997), and Synthetic Peptides: A User's Guide, edited by G. Grant (Oxford University Press, 2002).

The nucleic acid encoding a desired peptide may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate in which they are administered. Selection of the appropriate regulatory region or regions is a routine matter, within the level of ordinary skill in the art.

The compounds of the invention, whether prepared by chemical synthesis or recombinant DNA technology, may be purified using known techniques, for example preparative HPLC, FPLC, affinity chromatography, as well as other chromatographic methods. Isolated compounds may then be assessed for biological activity according to the methods described herein, as well as by any methods known to the skilled artisan.

Ocular Disorders Amenable to Treatment With Adiponectin Peptidomimetic Compounds The adiponectin peptidomimetic compounds described herein can be used to treat an ocular disease or disorder, including dry eye or an ocular disease associated with inflammation.

Dry eye disease or keratoconjunctivitis sicca (KCS) can be caused by or associated with various conditions including, but not limited to Sjogren syndrome, ocular cicatrical pemphigoid, congenital alacrima, blepharitis, lacrimal gland ablation, age-related lacrimal gland deficiency, alacrima (e.g., Triple A or Allgrove syndrome, and Riley-Day syndrome), lacrimal gland infiltration (e.g., sarcoidosis, lymphoma, and AIDS), lacrimal gland duct obstruction, meibomian gland disorder, pterygium, chronic inflammation of the conjunctiva, reflex block, herpes zoster, ocular allergies, autoimmune disease, chronic graft-versus-host disease, the natural aging process, diabetes, long-term contact lens wear, dry environment, excessive computer screen use, surgery that involves corneal incisions or ablates corneal nerves (e.g., cataract surgery, refractive surgery, retinal surgery, ocular tumor therapy, medications, decreased blinking (low blink rate), disorders of lid aperature or lid/globe dynamics, pregnancy, polycystic ovary syndrome, acne rosacea, lupus, scleraderma, sarcoidosis, Stevens-Johnson syndrome, Parkinson's disease, thyroid disease, cosmetic surgery, smoking, radiation therapy, vitamin A deficiency, and menopause.

Dry eye can also be caused by nutritional disorders and deficiencies, pharmacologic side effects, skin disease on and around the eyelids, eye stress and glandular and tissue destruction, environmental exposure to smog, smoke, excessively dry air, airborne particulates, autoimmune and other immunodeficient disorders. In dry eye, the ocular surface epithelium undergoes squamous metaplasia, manifested by loss of goblet cells, mucin deficiency and keratinization. These changes result in tear film instability, which leads to the clinical symptoms of dry eye syndrome.

Symptoms of dry eye include stinging, burning or scratchy sensation in the eye; ocular dryness or grittiness; stringy mucus in or around the eye; increase eye irritation; eye fatigue; sensitivity to light (photophobia); eye redness; excessive tearing; episode of blurred vision; foreign body sensation in the eye; pain or soreness around or in the eye; inability to cry when emotionally stressed; decreased tolerance of an activity requiring sustained visual attention; and any combination thereof. Symptoms of dry eye can be quantified using, for example, in the Ocular Surface Disease index (OSDI) questionnaire, which lists 12 symptoms and grades each on a scale of 1-4. Clinical signs of dry eye can be assessed, for example, by performing impression cytology (e.g., ocular surface staining), measuring tear breakup time (TBUT), performing the Schirmer's test, performing a phenol red thread tear test, and measuring the components of tears (e.g., analysis of tear proteins or tear-film osmolarity). Elevated osmolarity (hyperosmolarity) may cause less regulation of tear film, more damage to the ocular surface, and in some cases, increased inflammation of the eye.

Ocular diseases associated with inflammation include, but are not limited to, uveitis, dry eye, keratitis, allergic eye disease, infectious keratitis, herpetic keratitis, corneal angiogenesis, lymphangiogenesis, uveitis, pterygium, retinitis, choroiditis, acute multifocal placoid pigment epitheliopathy, Behcet's disease, postsurgical corneal wound healing, conditions caused by laser, conditions caused by photodynamic therapy, wet and dry age-related macular degeneration (ARAM, conditions affecting the posterior part of the eye, maculopathies, retinal degeneration, non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi and Harada syndrome, retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease, sympathetic ophthalmia, uveitic retinal disease, retinal detachment, trauma, conditions caused by photodynamic therapy, photocoagulation, hypoperfusion during surgery, radiation retinopathy, and bone marrow transplant retinopathy, proliferative vitreal retinopathy and epiretinal membranes, proliferative diabetic retinopathy, ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, myiasis, retinitis pigmentosa, systemic disorders with accosiated retinal dystrophies, congenital stationary night blindness, cone dystrophies, Stargardt's disease, fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum; retinal detachment, macular hole, giant retinal tear, retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors, other diseases affecting the posterior part of the eye, punctate inner choroidopathy, acute posterior multifocal placoid pigment epitheliopathy, myopic retinal degeneration, acute retinal pigment epitheliitis, postsurgical corneal inflammation, corneal transplantation, blepharitis, MGD, glaucoma, ocular hypertension, branch vein occlusion, retinal diseases, Best's vitelliform macular degeneration, retinitis pigmentosa, proliferative vitreoretinopathy (PVR), and any other degenerative diseases of either the photoreceptors or the retinal pigment epithelial (RPE).

Symptoms or clinical signs of ocular diseases associated with inflammation include, but are not limited to, unstable tear film, chronic hyperosmolar stress, evaporative tear loss, decreased lubricity, other tear deficiencies that lead to an increased in pro-inflammatory response in the eye, inflammation, and any combination thereof.

Pharmaceutical Compositions

The adiponectin peptidomimetic compounds can be used and formulated into any of a number of pharmaceutical compositions, including those described in the United States Pharmacopeia (U.S.P.), Goodman and Gilman's The Pharmacological Basis of Therapeutics, IO.sup.th Ed., McGraw Hill, 2001; Katzung, Ed., Basic and Clinical Pharmacology, McGraw-Hill/Appleton & Lange, 8th ed., Sep. 21, 2000; Physician's Desk Reference (Thomson Publishing; and/or The Merck Manual of Diagnosis and Therapy, 18th ed., 2006, Beers and Berkow, Eds., Merck Publishing Group; or, in the case of animals, The Merck Veterinary Manual, 9th ed., Kahn Ed., Merck Publishing Group, 2005.

Ophthalmic pharmaceutical compositions may also contain one or more excipients or other substances, such as preservatives, antioxidants, pH adjusting agents, buffering agents, gelling agents, viscosity enhancers, surfactants, solubility agents, lubricating agents, salts, co-solvents, diluents, carriers, adjuvants, oils, humectants, emollients, stabilizers, emulsifying agents, and/or dispersing agents. Other agents may be employed in the compositions for a variety of purposes. By way of example, injectable compositions may contain various excipients or other substances, such as preservatives, antioxidants, pH adjusting agents, buffering agents, salts, emulsifying agents, and/or dispersing agents.

Non-limiting examples of a preservative such as a water-soluble preservative include sodium bisulfite, sodium sulfate, sodium thiosulfate, benzalkonium chloride, chlorobutanol, thimerosal, ethyl alcohol, methylparaben, polyvinyl alcohol, benzyl alcohol, and phenylethyl alcohol.

Examples of ophthalmically acceptable antioxidants include, but are not limited to, sodium bisulfite, sodium thiosulfate, acetyl cysteine, cysteine, thioglycerol, sodium sulfite, acetone sodium bisulfite, dithioerythreitol, dithiothreitol, thiourea, and erythorbic acid.

Examples of ophthalmically acceptable pH adjusting agents, such as an acid, base and/or buffer include but are not limited to, an acid such as acetic, boric, citric, lactic, phosphoric, sulfuric, and hydrochloric acids, a base such as sodium hydroxide, sodium phosphate, sodium borate, sodium citrate, sodium acetate, sodium lactate and tris-hydroxymethylarainomethane, triethanolamine; and/or a buffer such as citrate/dextrose, sodium bicarbonate and ammonium chloride or an amino acid. These may be used alone and two or more used in combination. Such an acid, base and/or buffer can be included in an amount sufficient to adjust pH of the composition to an ophthalmically acceptable range.

The composition can be formulated for topical ophthalmic application, for example, in the form of solutions, ointments, creams, lotions, eye ointments and, most preferably, eye drops or eye gels and can contain the appropriate conventional additives, including, for example, preservatives, solvents to assist drug penetration, and emollients in ointments and creams. The ophthalmic vehicles include, but are not limited to, saline solution, water polyethers such as polyethylene glycol, polyvinyls such as polyvinyl alcohol and povidone, cellulose derivatives such as methylcellulose and hydroxy propyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

Solutions of the active compounds as free base or pharmacologically acceptable salt can be prepared in water suitably mixed with a surfactant, such as hydroxypropylcellulose, Tyloxapol, Poloxomer 188, Poloxomer 407, Tween 80, PEG 40, hydrogenated Castor oil, PEG35 Castor oil, and PEG40 stearate, and combinations thereof. The surfactant amount typically is between about 0.0001% (wt) and about 10% (wt), between about 0.001% (wt) and about 10% (wt), between about 0.01% and about 10% (wt), between about 0.05% (wt) and about 10% (wt), between about 0.075% (wt) and about 10% (wt), between about 0.1% (wt) and about 10% (wt), between about 1.0% and about 90% (wt), between about 10% and about 90% (wt), between about 1% and about 20% (wt), between about 5%, and about 20% (wt), between about 10% (wt) and about 20% (wt), between about 0.05% (wt) and about 15% (wt), between about 0.05% (wt) and about 14% (wt), between about 0.05% (wt) and about 13% (wt), between about 0.05% (wt) and about 12% (wt), between about 0.05% (wt) and about 11% (wt), between about 0.05% (wt) and about 10% (wt), between about 0.05% (wt) and about 90% (wt), between about 0.05% (wt) and about 8% (wt), between about 0.05% (wt) and about 7% (wt), between about 0.05% (wt) and about 6% (wt), between about 0.05% (wt) and about 5% (wt), between about 0.05% (wt) and about 4% (wt), between about 0.05% (wt) and about 3% (wt), between about 0.05% (wt) and about 2% (wt), and preferably between about 0.05% (wt) and about 0.1% (wt), in liquid formulations. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Alternatively, the compounds can be formulated for injection into the eye, such as intravitreal injection subj conjunctival injection and injection into the anterior chamber of the eye. In other instances, the compounds may be in a form suitable for implantation use, e.g., as entrapped in microcapsules. The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). The compositions can be also in an ophthalmic depot formulation, such as for subconjunctival administration. The adiponectin peptidomimetics can be embedded in in a biocompatible pharmaceutically acceptable polymer or a lipid encapsulating agent. The depot formulations may be adapted to release all or substantially all the active material over an extended period of time. The polymer or lipid matrix, if present, may be adapted to degrade sufficiently to be transported from the site of administration after release of all or substantially all the active agent. The depot formulation can be a liquid formulation, comprising a pharmaceutical acceptable polymer and a dissolved or dispersed active agent, upon injection, the polymer forms a depot at the injections site, e.g., by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion generally comprise polymers and can be bioerodible or non-bioerodible.

Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for ocular use. Suitable excipients, include but are not limited to propylene glycol, glycerol, PEG400, and polypropylene glycol, and combinations thereof. The excipient amount typically is between about 0.0001% (wt) and about 90% (wt), between about 0.001% (wt) and about 90% (wt), between about 0.01% and about 90% (wt), between about 0.1% (wt) and about 90% (wt), between about 1.0% and about 90% (wt), between about 10% and about 90% (wt), between about 1% and about 20% (wt), between about 5%, and about 20% (wt), between about 10% (wt) and about 20% (wt), between about 1% (wt) and about 15% (wt), between about 1% (wt) and about 14% (wt), between about 1% (wt) and about 13% (wt), between about 1% (wt) and about 12% (wt), between about 1% (wt) and about 11% (wt), between about 1% (wt) and about 10% (wt), between about 1% (wt) and about 9% (wt), between about 1% (wt) and about 8% (wt), between about 1% (wt) and about 7% (wt), between about 1% (wt) and about 6% (wt), between about 1% (wt) and about 5% (wt), between about 1% (wt) and about 4% (wt), between about 1% (wt) and about 3% (wt), between about 1% (wt) and about 2% (wt), and preferably between about 1.5% (wt) and about 10% (wt), in liquid formulations.

Alternatively, the active compounds may be applied to the eye via liposomes. Further, the active compounds may be infused into the tear film via a pump-catheter system. In some embodiments, the active compound is contained within a continuous or selective-release device, for example, membranes such as, but not limited to, those employed in the pilocarpine (Ocusert™) System (Alza Corp., Palo Alto, Calif.). In some embodiments, the active compounds is contained within, carried by, or attached to contact lenses which are placed on the eye. In other embodiments, the active compound is contained within a swab or sponge which can be applied to the ocular surface. In another embodiment, the active compound is contained within a liquid spray which can be applied to the ocular surface. In another embodiment, the active compound is injected directly into the lacrimal tissues or onto the eye surface.

When the pharmaceutical composition for treating dry eye is used as an ophthalmic solution, it is provided in any dosage form which is used for ophthalmic solution, for example, an aqueous eye drop such as aqueous ophthalmic solution, aqueous suspended ophthalmic solution, viscous ophthalmic solution and solubilized ophthalmic solution, or a non-aqueous ophthalmic solution such as non-aqueous ophthalmic solution and non-aqueous suspended ophthalmic solution. Among these, the aqueous ophthalmic solution is preferable.

When the pharmaceutical composition for treating dry eye is prepared into an aqueous ophthalmic solution, various additives normally used in the aqueous ophthalmic solution are conveniently contained therein as long as the object of the present invention is not adversely affected. Examples of such the additives include buffers, isotonizing agents, preservatives, solubilizers (stabilizers), pH adjusting agents, osmolarity adjusting agents, thickeners and chelating agents.

The buffers may be selected from, but not limited to, the group comprising a phosphate buffer, a borate buffer, a citrate buffer, a tartrate buffer, an acetate buffer (for example, sodium acetate) and an amino acid. The isotonizing agents may be selected from, but not limited to, the group comprising sugars such as sorbitol, glucose and mannitol, polyhydric alcohols such as glycerin, polyethylene glycol and polypropylene glycol, and salts such as sodium chloride. The preservatives may be selected from, but not limited to, the group comprising benzalkonium chloride, benzethonium chloride, alkyl paraoxybenzoates such as methyl paraoxybenzoate and ethyl paraoxybenzoate, benzyl alcohol, phenethyl alcohol, sorbic acid and salts thereof, thimerosal and chlorobutanol. The solubilizers (stabilizers) may be selected from, but not limited to, the group comprising cyclodextrin and derivatives thereof, water-soluble polymers such as polyvinylpyrrolidone), and surfactants such as polyethylene glycol, polypropylene glycol polysorbate 80 (trade name: Tween 80). The pH adjusting agents may be selected from, but not limited to, the group comprising hydrochloric acid, acetic acid, phosphoric acid, sodium hydroxide, potassium hydroxide and ammonium hydroxide. The thickeners may be selected from, but not limited to, the group comprising hydroxyethylcellulose, hydroxypropylcellulose, methylcellulose, hydroxypropylmethylcellulose and carboxymethylcellulose and salts thereof. The chelating agents may be selected from, but not limited to, the group comprising sodium edetate, sodium citrate and sodium condensed phosphate.

For ophthalmic application, preferably solutions are prepared using a physiological saline solution as a major vehicle. The pH of such ophthalmic solutions should preferably be maintained between 4.5 and 8.0; about 5 to 7.5; preferably 6 to 7 with an appropriate buffer system, a neutral pH being preferred but not essential. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. Salts and buffers include citrate/dextrose, sodium bicarbonate, ammonium chloride and mixtures of the aforementioned acids and bases.

The osmotic pressure of the aqueous ophthalmic composition is generally from about 200 to about 400 milliosmolar (mOsM), preferably from 260 to 340 mOsM, more preferably from 280 to 310 mOsm/kg. The osmotic pressure can be adjusted by using appropriate amounts of physiologically and ophthamologically acceptable ionic or non-ionic agents. Sodium chloride is a preferred ionic agent, and the amount of sodium chloride ranges from about 0.01% to about 1% (w/v), and preferably from about 0.05% to about 0.45% (w/v). Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can be used in addition to or instead of sodium chloride to achieve osmolality within the above-stated range. Further, non-ionic agents such as mannitol, dextrose, sorbitol, glucose and the like can also be used to adjust the osmolality.

Tonicity adjusters may be added as needed or convenient. They include, but are not limited to, salts, particularly sodium chloride, potassium chloride, mannitol and glycerin, or any other suitable ophthalmically acceptable tonicity adjuster. Various buffers and means for adjusting pH may be used so long as the resulting preparation is ophthalmically acceptable. Accordingly, buffers include acetate buffers, citrate buffers, phosphate buffers and borate buffers. An ophthalmically acceptable antioxidant for use in the present invention includes, but is not limited to, sodium metabi sulfite, sodium thiosulfate, acetylcysteine, butylated hydroxyanisole and butylated hydroxytoluene.

When the pharmaceutical composition for treating dry eye is prepared into an ophthalmic ointment, a base compound must be present. The base of the ophthalmic ointment may be selected from but not limited by the group comprising purified lanolin, VASELINE® plastibase, liquid paraffin and polyethylene glycol.

The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. Surfactants can include, but are not limited to Tyloxapol, Poloxomer 188, Poloxomer 407, Tween 80, PEG 40, hydrogenated Castor oil, PEG35 Castor oil, and PEG40 stearate alone and in combinations thereof. A preferred surfactant can be, for example, Tyloxapol, Poloxomer 188 and Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

The adiponectin peptidomimetic compounds can be formulated into lipid-based nanocarriers, such as solid lipid nanoparticles, nanostructured lipid carriers, lipid-drug conjugates, and coated-liposomes.

The formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five unit doses, where a typical unit dose is from one to about 8 drops, preferably one to about 3 drops. The volume of one drop usually is about 20-35 μl.

The formulations may be in the form of a sterile solution or suspension. The solution or suspension can be for topical or injectable application. It can be in a sterile injectable formulation, e.g., a liquid or suspension formulation. In some embodiments, it may be formulated according to known methods using suitable dispersing or wetting agents and suspending agents. The sterile injectable preparation may also be a sterile injectable solution or suspension in a non-toxic intraocularly- or intravitreally-acceptable diluent or solvent. Buffers, preservatives, antioxidants, and the like can also be incorporated as required.

Methods of Administration

The composition provided herein can be administered to the eye. In some embodiments, the composition is applied to the palpebral part of the eye, such as the external portion of the upper and lower eyelids and the medial and lateral canthus, and/or the ocular surface of the eye. In some instances, the compositions can be administered to an afflicted eye conjunctival sac. In sonic embodiments, the composition is administered topically, by intravitreal injection, by subconjunctival injection, by conjunctival injection, by intramuscular injection, by subcutaneous injection, by intravenous injection, by intracameral injection, or by implantation into the subject's eye. In some cases, administration includes intravitreal depot implantation or other ophthalmic drug delivery methods described in, e.g., Edelhauser et al., Invest Ophthalmol Vis Sci, 2010, 51(1145403-5420. The eye includes, but is not limited to, a tissue, gland, vessel, lens, muscle, nerve, or other structure in or around the eye such as an ocular tissue, ocular surface, ocular chamber, eyelid, nasolacrimal duct, meibomian gland, and lacrimal gland.

The composition can be formulated for ophthalmic application, for example, in the form of solutions, ointments, creams, lotions, eye ointments and, most preferably, eye drops or eye gels and can contain the appropriate conventional additives, including, for example, preservatives, solvents to assist drug penetration, and emollients in ointments and creams. Such topical formulations can contain compatible conventional carriers, for example cream or ointment bases, and ethanol or oleyl alcohol for lotions.

The composition can be administered to the eyes of a patient by any suitable means, but are preferably administered as a liquid or gel suspension in the form of drops, spray or gel. In one embodiment, the formulation is in the form of drops, and is dropped onto the ocular surface. In another embodiment, the formulation is contained within a swab or sponge which can be applied to the ocular surface. In another embodiment, the formulation is contained within a liquid spray or ointment which can be applied to the ocular surface. In another embodiment, the formulation is injected directly into the eye, such as into the lacrimal tissues or onto the eye surface. In a further embodiment, the formulation is first applied on a fingertip or other applicator, then applied or rubbed directly onto the lid margin or canthus. Alternatively, the adiponectin peptidomimetic compound can be applied to the eye via a colloidal dosage form such as nanoparticular, nanomicelles, liposomes, and microemulsions. Further, the composition can be infused into the tear film via a pump-catheter system. Another embodiment involves the adiponectin peptidomimetic compound contained within a continuous or selective-release device, for example, membranes. As an additional embodiment, the adiponectin peptidomimetic compound can be contained within, carried by, or attached to contact lenses or other compatible controlled release materials, which are placed on the eye or around the eye.

In some embodiments, the compositions are administered topically, intraocularly, intracamerally, intraorbitally, periocularly, intravitreally, subconjunctivally, conjunctivally, intramuscularly, subcutaneously, intravenously, intracamerally, or via other routes in or around the eye. Non-limiting delivery routes for the therapeutic compositions described herein include aqueous solution, oily solutions, e.g., ointments, colloidal carriers, e.g., micelles, emulsions, liposomes, nanoparticles, solids forms, e.g., collagen-based shields and/or particles, and drug-loaded punctual plugs, drug-loaded canalicular plugs, contact lenses, implants and inserts.

The suitability of a particular route of administration will depend in part on the pharmaceutical composition, its components, the disorder being treated, and the subject in need of the therapy.

Dosing

The dosage of a therapeutic agent administered to a subject will vary depending on a wide range of factors. For example, it would be necessary to provide substantially larger doses to humans than to smaller animals. The dosage will depend upon the size, age, sex, weight, medical history and condition of the subject, and the nature of the dry eye disease being treated, use of other therapies, the potency of the substance being administered, and the frequency of administration. The skilled artisan will be able to determine appropriate dosages depending on these and other factors. For example, when the therapeutic agent can be used as an ophthalmic solution for treating dry eye in a subject in need thereof, it can be desirable that the aqueous solution eye drop contain the therapeutic agent in an amount of about 0.001% (wt) to 30% (wt), e.g., about 0.001% (wt), about 0.005% (wt), about 0.01% (wt), about 0.02% (wt), about 0.03% (wt), about 0.04% (wt), about 0.05% (wt), about 0.06% (wt), about 0.07% (wt), about 0.08% (wt), about 0.09% (wt), about 0.1% (wt), about 0.2% (wt), about 0.3% (wt), about 0.4% (wt), about 0.5% (wt), about 0.6% (wt), about 0.7% (wt), about 0.8% (wt), about 0.9% (wt), about 1% (wt), about 2% (wt), about 3% (wt), about 4% (wt), about 5% (wt), about 6% (wt), about 7% (wt), about 8% (wt), about 9% (wt), about 10% (wt), about 11% (wt), about 12% (wt), about 13% (wt), about 14% (wt), about 15% (wt), about 16% (wt), about 17% (wt), about 18% (wt), about 19% (wt), about 20% (wt), about 21% (wt), about 22% (wt), about 23% (wt), about 24% (wt), about 25% (wt), about 26% (wt), about 27% (wt), about 28% (wt), about 29% (wt), about or 30% (wt). In some embodiments, the therapeutic agent can be in an amount ranging from about 0.001% (wt) to about 30% (wt), about 0.005% (wt) to about 30% (wt), about 0.01% (wt) to about 30% (wt), about 0.1% (wt) to about 30% (wt), about 1% (wt) to about 30% (wt), about 10% (wt) to about 30% (wt), about 20% (wt) to about 30% (wt), about 10% (wt) to about 20% (wt), about 0.001% (wt) to about 10% (wt), about 0.001% (wt) to about 1% (wt), about 0.001% (wt) to about 0.1% (wt), 0.01% (wt) to about 0.1% (wt), and the like. When administered, the therapeutic agent can be given once daily or with multiple daily doses such as twice per day, three times per day and four times per day. In some embodiments, the therapeutic agent can be administered once a day, every other day, or less frequently. The therapeutic agent can be administered when the subject has one or more symptoms of dry eye or an ocular disease. In some instances, the therapeutic agent can be given in a dose of one to five drops or more, for example, one drop, two drops, three drops, four drops, five drops or more. When administered, the compositions may be given once daily or with multiple daily doses such as twice per day, three times per day four times per day, five times per day or more. In some embodiments, the therapeutic agent can be administered less frequently then once daily. For instance, the therapeutic agent can be administered every week, every 2 weeks, every 3 weeks, every 4 weeks, every 6 weeks, every 7 weeks, every 8 weeks, or less frequently. In some embodiments, the therapeutic agent can be administered according to the severity of the symptoms experienced by the subject.

An effective amount of an adiponectin peptidomimetic compound will depend on the age, sex and weight of the patient, the current medical condition of the patient and the nature of the dry eye disease being treated. The skilled artisan will be able to determine appropriate dosages depending on these and other factors. For example, when the pharmaceutical composition is used as an ophthalmic solution for treating dry eye in a subject in need thereof, it is desirable that the aqueous solution eye drop contain the adiponectin peptidomimetic compound in an amount of about 0.0001% (wt) to 90% (wt), e.g., about 0.0001% (wt), about 0.0005% (wt), about 0.001% (wt), about 0.005% (wt), about 0.01% (wt), about 0.02% (wt), about 0.03% (wt), about 0.04% (wt), about 0.05% (wt), about 0.06% (wt), about 0.07% (wt), about 0.08% (wt), about 0.09% (wt), about 0.1% (wt), about 0.2% (wt), about 0.3% (wt), about 0.4% (wt), about 0.5% (wt), about 0.6% (wt), about 0.7% (wt), about 0.8% (wt), about 0.9% (wt), about 1% (wt), about 2% (wt), about 3% (wt), about 4% (wt), about 5% (wt), about 6% (wt), about 7% (wt), about 8% (wt), about 9% (wt), about 10% (wt), about 11% (wt), about 12% (wt), about 13% (wt), about 14% (wt), about 15% (wt), about 16% (wt), about 17% (wt), about 18% (wt), about 19% (wt), about 20% (wt), about 21% (wt), about 22% (wt), about 23% (wt), about 24% (wt), about 25% (wt), about 26% (wt), about 27% (wt), about 28% (wt), about 29% (wt), about), about 30% (wt), about 31% (wt), about 33% (wt), about 33% (wt), about 34% (wt), about 35% (wt), about 36% (wt), about 37% (wt), about 38% (wt), about 39% (wt), about 40% (wt), about 41% (wt), about 42% (wt), about 43% (wt), about 44% (wt), about 45% (wt), about 46% (wt), about 47% (wt), about 48% (wt), about 49% (wt), about 50% (wt), about 51% (wt), about 52% (wt), about 53% (wt), about 54% (wt), about 55% (wt), about 56% (wt), about 57% (wt), about 58% (wt), about 59% (wt), about 60% (wt), about 61% (wt), about 62% (wt), about 63% (wt), about 64% (wt), about 66% (wt), about 66% (wt), about 67% (wt), about 68% (wt), about 69% (wt about 70% (wt), about 71% (wt), about 72% (wt), about 73% (wt), about 74% (wt), about 75% (wt), about 76% (wt), about 77% (wt), about 78% (wt), about 79% (wt), about 80% (wt), about 81% (wt), about 82% (wt), about 83% (wt), about 84% (wt), about 85% (wt), about 86% (wt), about 87% (wt), about 88% (wt), about 89% (wt), about or 90% (wt). In some embodiments, the adiponectin peptidomimetic compound in an amount ranging from about 0.0001% (wt) to about 90% (wt), e.g., about 0.0001% (wt) to about 90% (wt), about 0.0010% (wt) to about 90% (wt), about 0.005% (wt) to about 90% (wt), about 0.01% (wt) to about 90% (wt), about 0.1% (wt) to about 90% (wt), about 1% (wt) to about 90% (wt), about 10% (wt) to about 90% (wt), about 20% (wt) to about 90% (wt), about 30% (wt) to about 90% (wt), about 40% (wt) to about 90% (wt), about 50% (wt) to about 90% (wt), about 60% (wt) to about 90% (wt), about 70% (wt) to about 90% (wt), about 80% (wt) to about 90% (wt), about 10% (wt) to about 50% (wt), about 10% (wt) to about 40% (wt), about 10% (wt) to about 30% (wt), about 10% (wt) to about 20% (wt), about 0.0001% (wt) to about 10% (wt), 0.0001% (wt) to about 1% (wt), 0.0001% (wt) to about 0.1% (wt), 0.0001% (wt) to about 0.01% (wt), 0.0001% (wt) to about 0.001% (wt), about 0.001% (wt) to about 10% (wt), about 0.001% (wt) to about 1% (wt), about 0.001% (wt) to about 0.1% (wt), 0.01% (wt) to about 0.1% (wt), 0.01% (wt) to about 10% (wt), and the like. When administered, the compositions can be given once daily or with multiple daily doses such as twice per day, three times per day and four times per day. In some embodiments, the compositions are administered once a day, every other day, or less frequently. The compositions can be administered when the subject has one or more symptoms of dry eye or an ocular disease. In some instances, the compositions are given in a dose of one to five drops or more, for example, one drop, two drops, three drops, four drops, five drops or more.

When the pharmaceutical composition is used as an ocular ointment, it is desirable that the ocular ointment contain the adiponectin peptidomimetic compound in an amount of about 0.0001% (wt) to 90% (wt), e.g., about 0.0001% (wt), about 0.0005% (wt), about 0.001% (wt), about 0.005% (wt), about 0.01% (wt), about 0.02% (wt), about 0.03% (wt), about 0.04% (wt), about 0.05% (wt), about 0.06% (wt), about 0.07% (wt), about 0.08% (wt), about 0.09% (wt), about 0.1% (wt), about 0.2% (wt), about 0.3% (wt), about 0.4% (wt), about 0.5% (wt), about 0.0% (wt), about 0.7% (wt), about 0.8% (wt), about 0.9% (wt), about 10% (wt), about 2% (wt), about 3% (wt), about 4% (wt), about 5% (wt), about 6% (wt), about 7% (wt), about 8% (wt), about 9% (wt), about 10% (wt), about 11% (wt), about 12% (wt), about 13% (wt), about 14% (wt), about 15% (wt), about 16% (wt), about 17% (wt), about 18% (wt), about 19% (wt), about 20% (wt), about 21% (wt), about 22% (wt), about 23% (wt), about 24% (wt), about 25% (wt), about 26% (wt), about 27% (wt), about 28% (wt), about 29% (wt), about), about 30% (wt), about 31% (wt), about 33% (wt), about 33% (wt), about 34% (wt), about 35% (wt), about 36% (wt), about 37% (wt), about 38% (wt), about 39% (wt), about 40% (wt), about 41% (wt), about 42% (wt), about 43% (wt), about 44% (wt), about 45% (wt), about 46% (wt), about 47% (wt), about 48% (wt), about 49% (wt), about 50% (wt), about 51% (wt), about 52% (wt), about 53% (wt), about 54% (wt), about 55% (wt), about 56% (wt), about 57% (wt), about 58% (wt), about 59% (wt), about 60% (wt), about 61% (wt), about 62% (wt), about 63% (wt), about 64% (wt), about 66% (wt), about 66% (wt), about 67% (wt), about 68% (wt), about 69% (wt), about 70% (wt), about 71% (wt), about 72% (wt), about 73% (wt), about 74% (wt), about 75% (wt), about 76% (wt), about 77% (wt), about 78% (wt), about 79% (wt), about 80% (wt), about 81% (wt), about 82% (wt), about 83% (wt), about 84% (wt), about 85% (wt), about 86% (wt), about 87% (wt), about 88% (wt), about 89% (wt), about or 90% (wt). In some embodiments, the adiponectin peptidomimetic compound in an amount ranging from 0.0001% (wt) to about 90% (wt), e.g., about 0.0001% (wt) to about 90% (wt), about 0.001% (wt) to about 90% (wt), about 0.005% (wt) to about 90% (wt), about 0.01% (wt) to about 90% (wt), about 0.1% (wt) to about 90% (wt), about 1% (wt) to about 90% (wt), about 10% (wt) to about 90% (wt), about 20% (wt) to about 90% (wt), about 30% (wt) to about 90% (wt), about 40% (wt) to about 90% (wt), about 50% (wt) to about 90% (wt), about 60% (wt) to about 90% (wt), about 70% (wt) to about 90% (wt), about 80% (wt) to about 90% (wt), about 10% (wt) to about 50% (wt), about 10% (wt) to about 40% (wt), about 10% (wt) to about 30% (wt), about 10% (wt) to about 20% (wt), about 0.0001% (wt) to about 10% (wt), 0.0001% (wt) to about 1% (wt), 0.0001% (wt) to about 0.1% (wt), 0.0001% (wt) to about 0.01% (wt), 0.0001% (wt) to about 0.001% (wt), about 0.001% (wt) to about 10% (wt), about 0.001% (wt) to about 1% (wt), about 0.001% (wt) to about 0.1% (wt), 0.01% (wt) to about 0.1% (wt), 0.01% (wt) to about 1% (wt), and the like. When administered, the compositions may be given once daily or with multiple daily doses such as twice per day, three times per day four times per day, 5 times per day or more. In some embodiments, the compositions are administered less frequently then once daily. For instance, the compositions can be administered every week, every 2 weeks, every 3 weeks, every 4 weeks, every 6 weeks, every 7 weeks, every 8 weeks, or less frequently. In some embodiments, the compositions are administered according to the severity of the symptoms experienced by the subject.

For adiponectin peptidomimetics administered topically, e.g., as eye drops or ointments, or for intraorbital or perioocular injection, exemplary dosages are in the range from about 0.001 to about 100 mg, e.g., in the range from about 0.1 to about 10 mg, for instance, applied once a day, twice a day, or more frequently. For ADP 355 administered topically, e.g., as eye drops or ointments, or for intraorbital or perio-ocular injection, exemplary dosages can be from about 0.01 mg/ml to about 200 mg/ml.

Having indicated that there is variability in terms of dosing, it is believed that those skilled in the art can determine appropriate dosing by administering relatively small amounts and monitoring the patient for therapeutic effect. If necessary, incremental increases in the dose can be made until the desired results are obtained. Generally, treatment is initiated with smaller dosages which may be less than the optimum dose of the therapeutic agent. Thereafter, the dosage is increased by small increments until the optimum effect under circumstances is reached. The total daily dosage can be divided and administered in portions during the day if desired.

The pharmaceutical preparation can be packaged or prepared in unit dosage form. In such form, the preparation is subdivided into unit doses containing appropriate quantities of the active component, e.g., according to the dose of the therapeutic agent. The unit dosage form can be a packaged preparation, the package containing discrete quantities of preparation. The composition can, if desired, also contain other compatible therapeutic agents.

The invention provides methods of treating and/or ameliorating dry eye or an ocular disease associated with inflammation in a subject in need thereof. The course of treatment is best determined on an individual basis depending on the particular characteristics of the subject. The treatment can be administered to the subject on a daily, twice daily, thrice daily, every other day, bi-weekly, weekly, monthly or any applicable basis that is therapeutically effective. The treatment can be administered alone or in combination with at least one other therapeutic agent, e.g., targeting the same ocular disorder or a related symptom. The additional agent can be administered simultaneously with the adiponectin peptidomimetic compound, at a different time, or on an entirely different therapeutic schedule (e.g., the adiponectin peptidomimetic compound can be administered daily, while the additional agent is weekly).

Co-Administration With a Therapeutic Agent

In some embodiments, the methods provided herein include coadministration of the adiponectin peptidomimetic compound with one or more additional therapeutic agents. The term "coadministration" refers to administration of a first amount of an adiponectin peptidomimetic compound or a pharmaceutically acceptable salt thereof and a second amount of at least one other therapeutic agent, e.g., another therapeutic agent for treating an ocular disease, or a therapeutic agent to address associated symptoms, e.g., inflammation. In some instances, the adiponectin peptidomimetic compound and the other therapeutic agent are administered simultaneously or essentially simultaneously. The adiponectin peptidomimetic compound and the other therapeutic agent may be in a single pharmaceutical composition, or in multiple pharmaceutical compositions. In other instances, the adiponectin peptidomimetic compound and the other therapeutic agent are administered sequentially. In a sequential dosing, the adiponectin peptidomimetic compound and the other therapeutic agent are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. The combined administration includes coadministration, using separate formulations or a single pharmaceutical formulation, and consecutive administration in either order, wherein preferably there is a time period while both (or all) active agents simultaneously exert their biological activities.

In some embodiments, the one or more additional therapeutic agents include, punctual plugs, topical steroids topical tetracyclines, topical nonsteroidal anti-inflammatory drugs (NSAMS, such as topical diclofenac and topical ketorolac), IL-1 antagonists, other inflammatory pathway antagonists or inhibitors, angiostatic peptides, angiostatic steroids, modulators/inhibitors of VEGF or FGF, glucocorticosteroids, leukotriene modulators, anti-histamines, cytokine modulators/inhibitors, growth factor modulators/inhibitors, T-cell inhibitors, oral or topical pilocarpine, vitamin A, tretinoin (e.g., all trans-retinoic acid), doxycycline, cyclosporine A (e.g., RESTASIS® (Allergan), azithromycin, mucin stimulants (e.g., Diquafasol (inspire Pharmaceuticals) 15-(S)-HETE (Alcon), rebamipide (Otsuka) and ecabet (ISTA)), hormonal agents and lacrimal gland stimulants (e.g., androgen tears (Allergan)) and a tear substitute (e.g., artificial tears). In some cases, the compositions described herein are administered in combination with progesterone, synthetic progestogens, medroxyprogesterone acetate, norethindrone, norethindrone acetate, megestrol acetate, 17-a-hydroxyprogesterone caproate, norgestrel, and derivatives thereof. Additional therapeutic agents include lifitegrast, EBI-005 (Eleven Biotherapeutics), anakinra (Amgen), MIM-D3 (Mimitogen Pharmaceuticals), rebamipide (Otsuka Pharmaceuticals), tofacitinib (Pfizer), dexamethasone phosphate (EyeGate Pharmaceuticals), RGN-259 (RegeneRx), KPI-121 (loteprednol etabonate; Kala Pharmaceuticals), bromfenac (ISTA Pharmaceuticals), diquafosol tetrasodium (Merck and Co., Inc.), hydroxychloroquine (Sanofi-Aventis), rebamipide (Acucela Inc.), CFI01 (Can-Fite Bio-Pharma), lifitegrast (Shire), EBI-005 (Eleven Biotherapeutics), cyclosporine (haporine-S; DH Bio Co., Ltd.), rimexolone (Alcon Research), ecabet sodium (Bausch & Lomb Incorporated), rituximab (IDEC Pharmaceuticals), tocilizumab (Hoffman-La Roche Ltd.), skQI (Mitotech, SA), cis-UCA (Herantis Pharma PLC). LME636 (Alcon Research), AGN-223575 (Allergan), ISV-101 (InSite Vision), OTX-DP (Ocular Therapeutix, Inc.), rivoglitazone (Suiten Pharmaceutical Co.), mapracorat (Bausch & Lomb Incorporated), resolvin (Resolvyx), tasocitinib/tofacitinib (Pfizer), RU-101 (R-Tech Ueno, Ltd.), DNase (Genentech, Inc.), voclosporin (Lux Biosciences), P-321 (Pari on Sciences), ACCS (Stemnion, Inc.), AGN-23241 1 (Allergan), and those described in, e.g., Ridder and Karsolia, Clinical Optometry, 2015, 2015(7):91-102.

Lifitegrast is a small-molecule that inhibits the integrin, lymphocyte function-associated antigen 1 (LFA-1), a cell surface protein found on leukocytes. Lifitegrast can bind to LFA-1 which blocks LFA-1 from interacting with its cognate ligand, intercellular adhesion molecule 1 (ICAM-1). This mechanism down-regulates inflammation mediated by T lymphocytes.

The combination of an adiponectin peptidomimetic compound with another therapeutic agent can result in an enhanced efficacy in the treatment of ocular diseases. Administration of the active agents individually, consecutively, simultaneously, in combination or on an entirely different schedule as compared to the administration for either active agent individually can result in greater anti-inflammatory activity and improved clinical efficacy. A synergistic effect can also be observed. The synergy can allow for reduced dosages of the active agents when administered either individually, consecutively, simultaneously, in combination or on an entirely different schedule as compared to the dosages for either active agent individually. The reduced dosage can help reduce any side effects that may appear. Accordingly, in combination therapy, the effective amount of the additional (second) therapeutic agent and the effective amount of the adiponectin peptidomimetic compound are together effective to reduce the symptoms/effects of an ocular disease.

One of skill in medicine can best determine the appropriate dose of the additional therapeutic agent by considering the state of the patient, the recommended dose, the severity of disease, and the efficacy of administering the combination of the adiponectin peptidomimetic compound with the therapeutic agent. Synergistic effects resulting from the administering the combination of the adiponectin peptidomimetic compound with the therapeutic agent can also result.

Methods of Determining Therapeutic Efficacy

A variety of methods can be performed evaluate a subject's treatment response to the compositions provided herein. In some instances, an assay, test or measurement can be made to determine whether methods described herein have alleviated at least one symptom or clinical sign of dry eye or an ocular disease associated with inflammation. Detailed descriptions of methods for measuring or evaluating symptoms or clinical signs of dry eye or an ocular disease provided herein are found in, for example, Pult et al., Eye (Lond), 2011, 25(4): 502-510, Bhatnagar et al., Int J Opthalmol, 2015, 8(1): 174-81, Messmer, Dtsch Arztebl Int, 2015, 112(5): 71-82.

Changes in tear secretion can be assessed by the Schirmer's test, phenol red thread tear test (PRTT) and other methods of determining the rate and quantity of tear production. Changes in tear clearance can be assessed by fluorescein clearance test and fluorophotometry. Ocular surface damage and corneal epithelial defects can be evaluated vital dye staining, e.g., fluorescein, rose bengal, and lissamine green staining. Cytology of the ocular surface can be analyzed by impression cytology, brush cytology, flow cytometry, and confocal microscopy. Tear film stability can be looked at by analyzing tear break-up time, using the Tear film Stability Analysis System (TSAS), wavefront aberrometry, laser scanning microscopy, functional visual acuity, and tear film interferometry. Tear volume change can be assessed by tear meniscus measurement. Lipid layer changes to tear film can be assessed by tear film interferometry, meibometry, and meibography. Tear evaporation assessment can be made by evaporimeter, closed chamber, and ventilated chamber. Improvements in tear film chemical properties can be assessed by tear osmolarity, depression of freezing point, vapor pressure osmometry, and conductivity (Ocusense). Biochemical analysis of tear composition may include mucin and lipid analyses. Improvement in the ocular surface can be visualized by using dyes (such as fluorescein, lisamine green or rose bengal and observing less irregular morphology and staining of the conical or conjunctival epithelium, compared to baseline.

The alleviation of at least one symptom or a clinical sign of an ocular disease, such as dry eye and an ocular disease associated with inflammation, can be determined by comparing the degree of the symptom or clinical sign after treatment to the degree of the same symptom or clinical sample prior to treatment. If the degree of the symptom or clinical sign has decreased after treatment, then an improvement or alleviation can be indicated.

EXAMPLES

Example 1

Vehicle was prepared by dissolving propylene glycol (1.77 g) and Tyloxapol (0.1 g) in 97 mL of 35 mM of Acetic Acid/Sodium Acetate buffer, pH 4.3-4.5 by mixing until uniform. The peptide D-Asn-Ile-Pro-Nva-Leu-Tyr-D-Ser-Phe-Ala-D-Ser-NH$_2$ (API, also referred to as ALY688 or ALY-688 herein) (1.0 g) was added to the vehicle and mixed until dissolved. The pH was adjusted with small amounts of Acetic Acid or Sodium Hydroxide. The formulation was sterile-filtered.

The formulation of Example 1 provided stability of the active pharmaceutical ingredient and potential for minimal irritation. The solubility of the peptide was significantly increased. A concentration of 12 mg/g Acetate buffer gave a clear solution at a pH 4.5.

Proceeding as in Example 1 the following formulations were prepared (all percentages are wt percentages):

| Formula 1 | |
|---|---|
| API | 1.00% |
| Propylene Glycol | 1.72% |
| Poloxamer 188 | 0.10% |
| Acetic Acid | 0.11% |
| Sodium Acetate | 0.09% |
| Water | 96.97% |
| Total | 100.00% |

| Formula 2 | |
|---|---|
| API | 0.51% |
| Propylene Glycol | 1.73% |
| Poloxamer 188 | 0.10% |
| Acetic Acid | 0.11% |
| Sodium Acetate | 0.09% |
| Water | 97.47% |
| Total, g | 100.00% |

| Formula 3 | |
|---|---|
| API | 0.25% |
| Propylene Glycol | 1.74% |
| Poloxamer 188 | 0.10% |
| Acetic Acid | 0.11% |

Formula 3

| | |
|---|---|
| Sodium Acetate | 0.09% |
| Water | 97.71% |
| Total, g | 100.00% |

Formula 4

| | |
|---|---|
| API | 0.50% |
| Propylene Glycol | 1.55% |
| Poloxamer 188 | 0.10% |
| Acetic Acid | 0.10% |
| Sodium Acetate | 0.24% |
| Water | 97.51% |
| Total | 100.00% |

Formula 5

| | |
|---|---|
| API | 1.00% |
| Propylene Glycol | 1.55% |
| Poloxamer 188 | 0.10% |
| Acetic Acid | 0.10% |
| Sodium Acetate | 0.24% |
| Water | 97.01% |
| Total | 100.00% |

Formula 6

| | |
|---|---|
| API | 0.50% |
| Propylene Glycol | 1.58% |
| Tyloxapol | 0.10% |
| Acetic Acid | 0.09% |
| Sodium Acetate | 0.24% |
| Water | 97.99% |
| Total | 100.00% |

Formula 7

| | |
|---|---|
| API | 1.00% |
| Propylene Glycol | 1.57% |
| Tyloxapol | 0.10% |
| Acetic Acid | 0.09% |
| Sodium Acetate | 0.24% |
| Water | 97.00% |
| Total | 100.00% |

Formula 8

| | |
|---|---|
| API | 0.50% |
| Propylene Glycol | 1.43% |
| Poloxamer 188 | 0.10% |
| Acetic Acid | 0.04% |
| Sodium Acetate | 0.34% |
| Water | 97.59% |
| Total | 100.00% |

Formula 9

| | |
|---|---|
| API | 0.50% |
| Propylene Glycol | 1.44% |
| Tyloxapol | 0.10% |
| Acetic Acid | 0.04% |
| Sodium Acetate | 0.34% |
| Water | 97.58% |
| Total | 100.00% |

Formula 10

| | |
|---|---|
| API | 1.00% |
| Propylene Glycol | 1.40% |
| Poloxamer 188 | 0.20% |
| Acetic Acid | 0.19% |
| Sodium Acetate | 0.30% |
| Water | 96.92% |
| Total | 100.00% |

Formula 11

| | |
|---|---|
| API | 1.00% |
| Propylene Glycol | 1.38% |
| Tyloxapol | 0.10% |
| Acetic Acid | 0.19% |
| Sodium Acetate | 0.30% |
| Water | 96.90% |
| Total | 100.00% |

Formula 12

| | |
|---|---|
| API | 1.00% |
| Propylene Glycol | 1.25% |
| Tyloxapol | 0.10% |
| Acetic Acid | 0.17% |
| Sodium Acetate | 0.41% |
| Water | 97.05% |
| Total | 100.00% |

Formula 13

| | |
|---|---|
| API | 1.00% |
| Propylene Glycol | 1.54% |
| Tyloxapol | 0.10% |
| Acetic Acid | 0.19% |
| Sodium Acetate | 0.14% |
| Water | 97.03% |
| Total | 100.00% |

Formula 14

| | |
|---|---|
| API | 0.80% |
| Propylene Glycol | 1.54% |
| Tyloxapol | 0.10% |
| Acetic Acid | 0.19% |

| Formula 14 | |
|---|---|
| Sodium Acetate | 0.14% |
| Water | 97.23% |
| Total | 100.00% |

| Formula 15 | |
|---|---|
| API | 0.50% |
| Propylene Glycol | 1.55% |
| Tyloxapol | 0.10% |
| Acetic Acid | 0.19% |
| Sodium Acetate | 0.14% |
| Water | 97.52% |
| Total | 100.00% |

| Formula 16 | |
|---|---|
| API | 0.50% |
| Propylene Glycol | 1.55% |
| Tyloxapol | 0.10% |
| Acetic Acid | 0.19% |
| Sodium Acetate | 0.14% |
| Water | 97.52% |
| Total | 100.00% |

| Formula 17 | |
|---|---|
| API | 1.00% |
| Propylene Glycol | 1.53% |
| Tyloxapol | 0.10% |
| Acetic Acid | 0.19% |
| Sodium Acetate | 0.14% |
| Water | 97.04% |
| Total | 100.00% |

| Formula 18 | |
|---|---|
| API | 1.00% |
| Propylene Glycol | 1.86% |
| Tyloxapol | 0.10% |
| Acetic Acid | 0.13% |
| Sodium Acetate | 0.10% |
| Water | 96.82% |
| Total | 100.00% |

| Formula 19 | |
|---|---|
| API | 1.00% |
| Propylene Glycol | 1.67% |
| Tyloxapol | 0.10% |
| Acetic Acid | 0.15% |
| Sodium Acetate | 0.11% |
| Water | 96.96% |
| Total | 100.00% |

| Formula 20 | |
|---|---|
| API | 1.00% |
| Propylene Glycol | 1.62% |
| Tyloxapol | 0.10% |
| Acetic Acid | 0.17% |
| Sodium Acetate | 0.13% |
| Water | 96.98% |
| Total | 100.00% |

Example 2

A stock solution containing 200 mM Boric Acid and 400 mM Mannitol was prepared and stirred for 2 hours to form a Boric Acid/Mannitol complex. Buffer (50 mL) was prepared by mixing 46.25 g of a 20 mM Acetic Acid/Sodium Acetate buffer with 3.75 g of the Boric Acid/Mannitol stock solution to achieve a buffer pH of 4.3-4.5. Vehicle (50 mL) was then prepared by mixing 48.29 g of the above buffer with Tyloxapol (0.05 g), Propylene Glycol (0.10 g) and additional Mannitol (1.58 g) for osmolality. The peptide D-Asn-Ile-Pro-Nva-Leu-Tyr-D-Ser-Phe-Ala-D-Ser-NH$_2$ (0.5 g) was added to this vehicle and mixed until a solution. The pH was adjusted with small amounts of Acetic Acid or Sodium Hydroxide, as needed. The entire formulation is sterile-filtered.

According to the procedure above, the following formulation was prepared:

| Formula 21 | |
|---|---|
| API | 0.401% |
| Propylene Glycol | 0.193% |
| Tyloxapol | 0.097% |
| Acetic Acid | 0.014% |
| Sodium Acetate | 0.138% |
| Boric Acid | 0.090% |
| Mannitol | 3.65% |
| Total | 100% |

According to a similar procedure, the following formulation can be prepared:

| Formula 22 | |
|---|---|
| API | 0.4% |
| Propylene Glycol | 0.193% |
| Tyloxapol | 0.097% |
| Acetic Acid | 0.015% |
| Sodium Acetate | 0.228% |
| Boric Acid | 0.090% |
| Mannitol | 3.53% |
| Total | 100% |

According to a similar procedure, the following formulation can be prepared:

| Formula 23 | |
|---|---|
| API | 0.1% |
| Propylene Glycol | 0.193% |
| Tyloxapol | 0.097% |

-continued

| Formula 23 | |
|---|---|
| Acetic Acid | 0.0065% |
| Sodium Acetate | 0.25% |
| Boric Acid | 0.090% |
| Mannitol | 3.6% |
| Total | 100% |

More generally, formulations of ophthalmic solution according to the following table can be prepared:

| Component | Quantity, w/w % |
|---|---|
| API | 0, 0.1, 0.4% |
| Boric Acid | 0.05 to 0.20% |
| D-Mannitol | 2.0-4.0% |
| Sodium Acetate | 0.25% |
| Acetic Acid (glacial) | 0.0063-0.0150% |
| Propylene Glycol | 0.193% |
| Tyloxapol | 0.07-0.097% |
| Water for Injection | Q.S. to volume |
| Sodium Hydroxide | as needed |
| Hydrochloric Acid | as needed |

Example 3

Irritation Studies

Irritation studies in rabbits were performed with Formulations 13, 14, 15, 16, 17, 18, 19, 20 and 21 and placebo. Formulations were found to be tolerated by test subjects.

Example 4

Effects of ALY688 on Atropine-Induced Dry Eye in Rabbits

The purpose of this study was to evaluate the efficacy of a topical ALY688 ophthalmic formulation according Formula 22 in Example 2 in a rabbit atropine-induced dry eye model.

Experimental Design

Clinical evaluations of corneal fluorescein staining, tear break-up time and tear volume were determined at five timepoints during the 14 day dosing period. Pre-dose ophthalmic anterior segment slit-lamp exams with corneal fluorescein staining, Tear Volume (TV) and Tear Break-Up Time (TBUT) assessments were performed. Animals were assigned to treatment groups such that the average baseline TV and TBUT values were approximately equal across groups.

Study Groups were assigned as follows:
Group 1: Atropine+ALY688 0.4% ophthalmic TID, (n=6)
Group 2: Atropine+Vehicle ophthalmic TID, (n=6)
Group 3: Atropine only (n=4)
Test article dosing began on Day −1.
Atropine eye drops (TID) began on Day 0.
Dry eye evaluations were performed on Days 1, 3, 7, 10, and 13.

Dosing and procedures were timed so that the interval between dosing and evaluations was consistent for all animals, and that procedures did not interfere with one another.

Methods

The evaluator was masked as to treatment group for all assessments.

Examinations: Slit-lamp examinations of the anterior segment were performed at baseline and on Day 13 according to the McDonald-Shattuck Scoring System including conjunctival congestion, swelling, and discharge, corneal opacity, pannus, anterior chamber cells and flare, iris, light reflex, and lens.

Tear Breakup Time (TBUT): TBUT was determined after instillation of 6 μL of 2% sodium fluorescein in sterile saline onto the lower eyelid. After manually blinking the eye, the time for black spots or streaks to appear on the cornea under cobalt filter illumination was recorded. The procedure was conducted three times consecutively, and the average of three readings was used.

Corneal epithelial staining: Corneal staining was assessed immediately after the TBUT measurement, after rinsing excess fluorescein. Fluorescein uptake was graded according to the NEI/Industry Grading System, in 5 separate areas of the cornea using a 0-3 grading scale maximum score: 15). Total staining score was calculated for each eye.

Tear Volume (TV): Tear volume was measured using Schirmer Tear Test strips (Intervet, Inc., Summit, NJ), by placing the strip into the lower fornix for 60 seconds and recording the mm distance of the wetted area.

Results

Ocular Exams: There were no abnormal findings at baseline or on Day 13 related to test article administration based upon anterior segment slit-lamp exam.

Corneal staining results are illustrated in connection with FIG. 1, where data are average±SEM for n=12 (ALY-688 and vehicle), or n=8 (atropine-only) eyes per group). At baseline, no corneal fluorescein staining was observed in any animal. During the dosing period, staining was lower in the ALY688 group than in the vehicle control group at all evaluation timepoints. On Days 1, 3, and 10, this difference was statistically significant ($p<0.05$). The ALY688 group was statistically significantly higher than the vehicle group on Day 7 ($p=0.01$), Day 10 ($p<0.001$), and Day 13 ($p=0.001$), and the atropine-only group on all post-baseline days (2-sample, two-tailed t-test).

Figure 2:
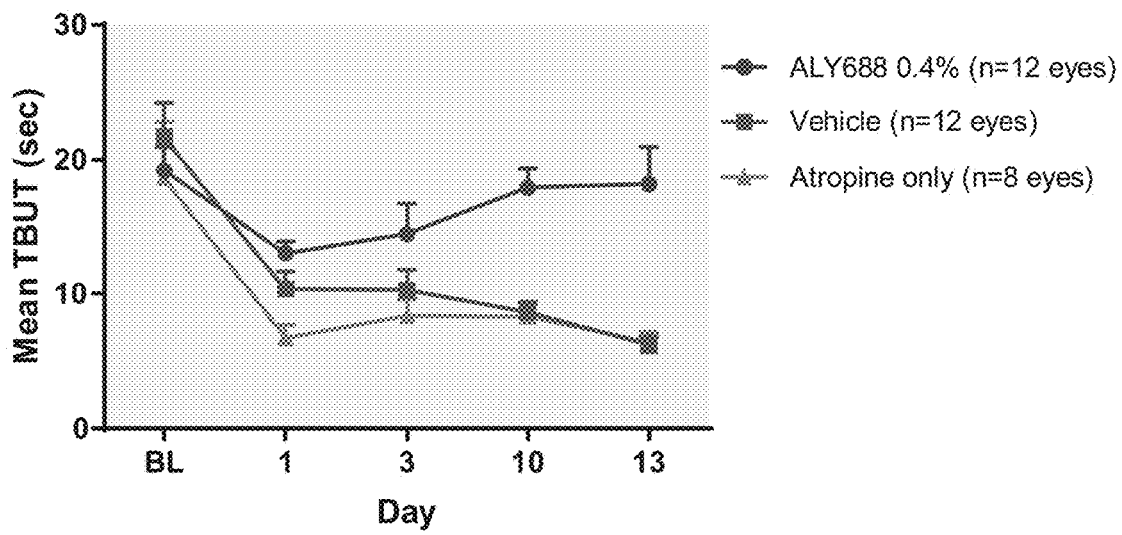
FIG. 2 shows Tear Break-Up Time (TBUT) results of the use of a formulation of the present invention in the eyes of test rabbits.

Tear Break-Up Time (TBUT) results are illustrated in connection with FIG. 2, where data are average±SEM for n=12 (ALY-688 and vehicle), or n=8 (atropine-only) eyes per group. TBUT decreased in all groups within 1 day of atropine treatment, but to a much lesser degree in the ALY-688 group (32% decrease on Day 1 vs. 50% decrease in the Vehicle group). By Day 7, the vehicle group continued to decline, while the ALY-688 group had returned to baseline TBUT levels. ALY688 maintained normal TBUT levels through the remainder of the study, with statistically significant higher TBUT compared to vehicle on Days 7, 10, and 13 ($p<0,01$). The ALY688 group was statistically significantly higher than the vehicle group on Day 7 ($p=0.01$), Day 10 ($p<0.001$), and Day 13 ($p=0.001$), and the atropine-only group on all post-baseline days (2-sample, two-tailed t-test).

Figure 3:
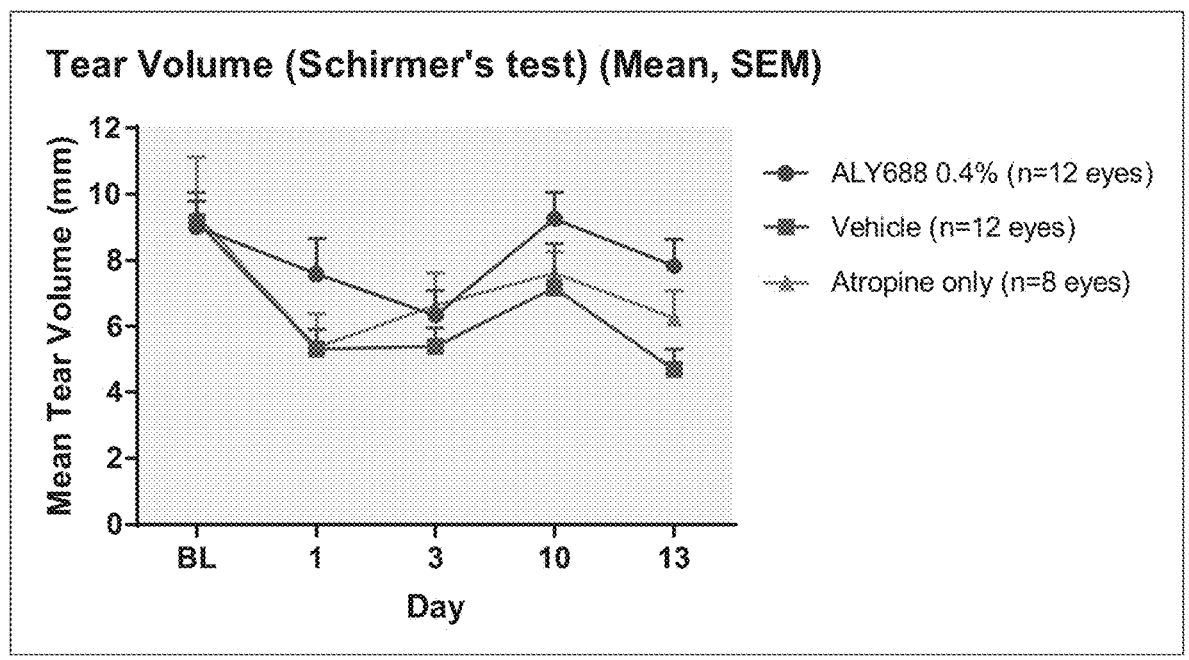
FIG. 3 shows Tear Volume (TV) results of the use of a formulation of the present invention in the eyes of test rabbits.

Tear Volume (TV) results are illustrated in connection with FIG. 3, where data are average±SEM for n=12 (ALY-688 and vehicle), or n=8 (atropine-only) eyes per group. TV decreased significantly subsequent to atropine dosing, but the ALY688 group remained consistently higher than the vehicle control group at all timepoints. This difference was statistically significant only on Day 13 ($p<0.01$). The variation in TV over the course of the experiment is attributed to the difference in the time of measurement relative to the previous atropine dose, with the TV measurements on Days 1, 3, and 13 performed 1.25 hours after atropine administration, and Day 7 and Day 10 measurements performed ~20 and 3.25 hours after atropine administration, respectively.

The ALL688 group was statistically significantly higher than the vehicle group on Day 13 (p=0.01), with borderline (p=0.08) significance on Days 1 and 7, (2-sample, two-tailed t-test).

Conclusion

Figure 4A:
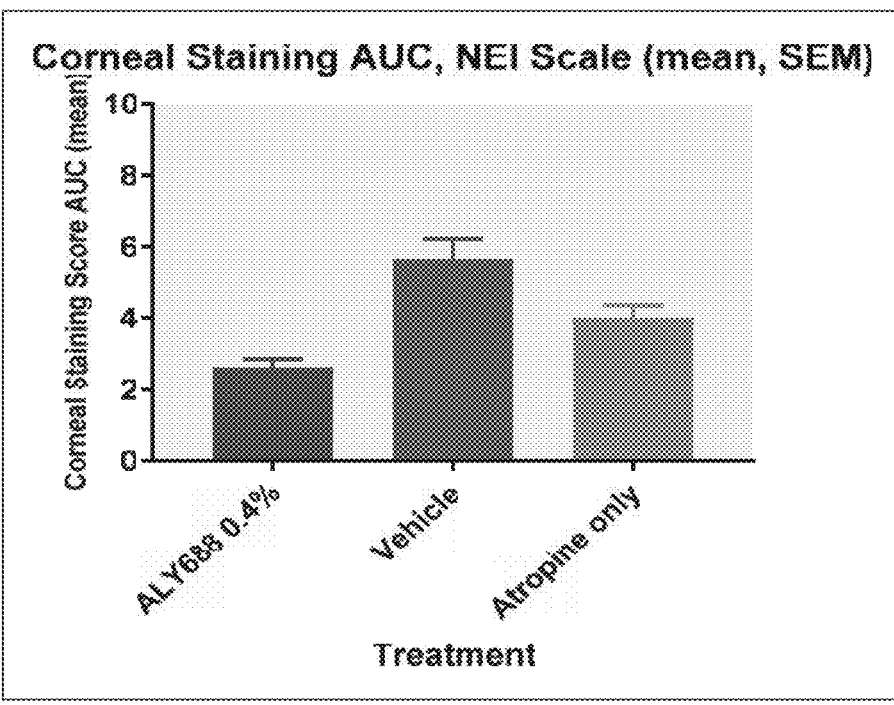
FIGS. 4A-4C show overall response versus baseline (integrated AUC response) for corneal staining, TBUT, and TV test results as illustrated in FIGS. 1-3.
Figure 4B:
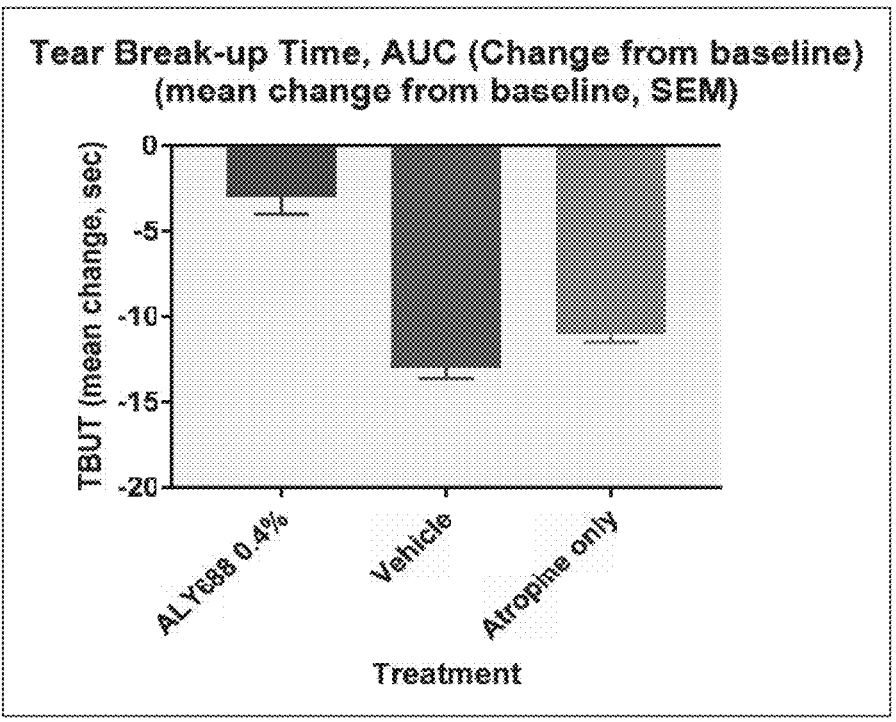
Figure 4C:
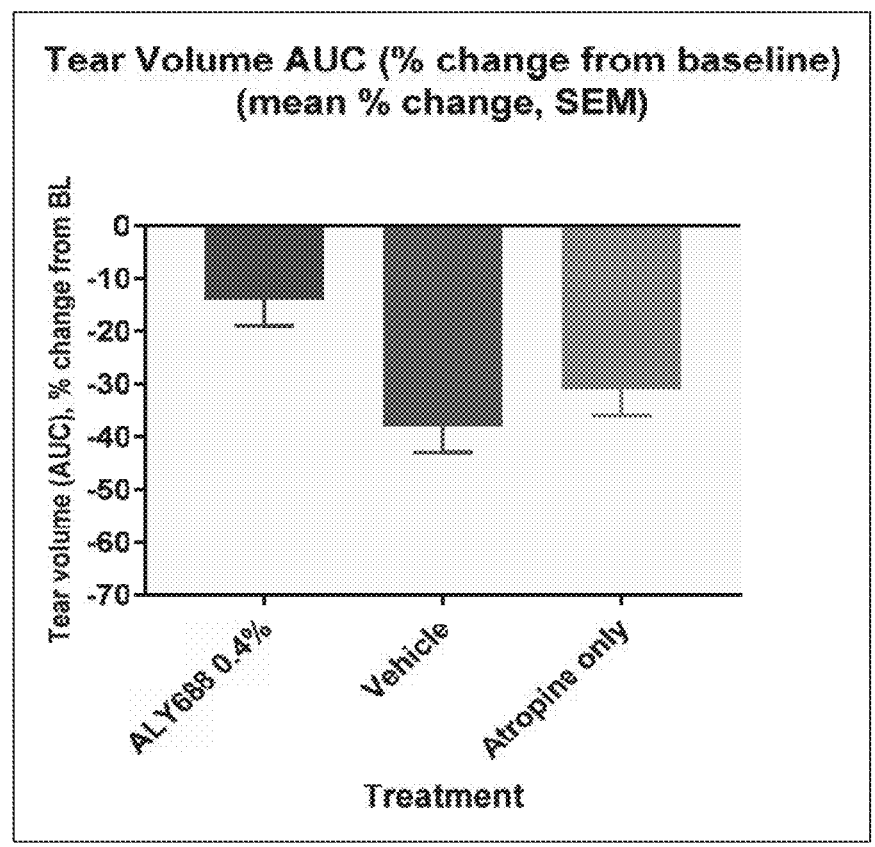

Overall, using an integrated analysis at all post-baseline timepoints, ALY688 showed a highly statistically significant improvement (p<0.005) compared to vehicle for each parameter (FIGS. 4A-4C).

- Atropine administration induced features of dry eye including: decreased tear volume and tear break-up time, and increased conical fluorescein staining. The timing of atropine administration can impact severity of signs.
- Topical ALY688 mitigated all of the assessed parameters of dry eye.
- Statistically significant improvements in tear volume, tear break-up time, and corneal fluorescein staining following ALY688 vs vehicle control was observed at multiple timepoints.
- This study demonstrated that ALY688 ophthalmic solution was highly effective at reducing dry eye signs in an atropine-induced model of disease in NZW rabbits. Effects were noted as early as two days after initiation of ALY688 treatment.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A composition comprising: a therapeutically effective amount of an adiponectin peptidomimetic having the formula of D-Asn-Ile-Pro-Nva-Leu-Tyr-D-Ser-Phe-Ala-D-Ser-NH$_2$, a generally recognized as safe solubilizer, one or more generally recognized as safe surfactants, a buffer comprising boric acid and mannitol; wherein the osmolality is between 260 to 330 mOsm/kg and the pH is between 4.5 to 5.5.

2. The composition of claim 1, wherein the solubilizer is selected from polypropylene glycol, glycerol, PEG400 and propylene glycol, the surfactant is selected from Polysorbate 80, Tyloxapol, Poloxamer, PEG 40 Hydrogenated Caster Oil, PEG 35 Caster Oil and PEG 40 Sterate, wherein the buffer further comprises an acetate buffer.

3. The composition of claim 2, comprising, by weight: 0.01% to 2% D-Asn-Ile-Pro-Nva-Leu-Tyr-D-Ser-Phe-Ala-D-Ser-NH$_2$, 1% to 2% propylene glycol, 0.08% to 0.12% Tyloxapol or Poloxamer, 0.02% to 0.20% acetic acid and 0.05% to 0.5% sodium acetate.

4. The composition of claim 3, comprising, by weight: 0.20% to 1.0% D-Asn-Ile-Pro-Nva-Leu-Tyr-D-Ser-Phe-Ala-D-Ser-NH$_2$, 1.20% to 1.90% propylene glycol, 0.10% Tyloxapol or Poloxamer, 0.04% to 0.20% acetic acid and 0.08% to 0.42% sodium acetate.

5. The composition of claim 4, selected from a composition comprising:
- 1.00% D-Asn-Ile-Pro-Nva-Leu-Tyr-D-Ser-Phe-Ala-D-Ser-NH$_2$, 1.77% propylene glycol, 0.10% Tyloxapol, 0.14% acetic acid and 0.08% sodium acetate;
- 0.5% D-Asn-Ile-Pro-Nva-Leu-Tyr-D-Ser-Phe-Ala-D-Ser-NH$_2$, 1.58% propylene glycol, 0.10% Tyloxapol, 0.09% acetic acid and 0.24% sodium acetate;
- 1.00% D-Asn-Ile-Pro-Nva-Leu-Tyr-D-Ser-Phe-Ala-D-Ser-NH$_2$, 1.57% propylene glycol, 0.10% Tyloxapol, 0.09% acetic acid and 0.24% sodium acetate;
- 0.5% D-Asn-Ile-Pro-Nva-Leu-Tyr-D-Ser-Phe-Ala-D-Ser-NH$_2$, 1.43% propylene glycol, 0.10% Tyloxapol, 0.04% acetic acid and 0.34% sodium acetate;
- 0.5% D-Asn-Ile-Pro-Nva-Leu-Tyr-D-Ser-Phe-Ala-D-Ser-NH$_2$, 1.44% propylene glycol, 0.10% Tyloxapol, 0.04% acetic acid and 0.34% sodium acetate;

1.00% D-Asn-Ile-Pro-Nva-Leu-Tyr-D-Ser-Phe-Ala-D-Ser-NH$_2$, 1.72% propylene glycol, 0.10% Poloxamer 188, 0.11% acetic acid and 0.09% sodium acetate;

0.51% D-Asn-Ile-Pro-Nva-Leu-Tyr-D-Ser-Phe-Ala-D-Ser-NH$_2$, 1.73% propylene glycol, 0.10% Poloxamer 188, 0.11% acetic acid and 0.09% sodium acetate;

0.25% D-Asn-Ile-Pro-Nva-Leu-Tyr-D-Ser-Phe-Ala-D-Ser-NH$_2$, 1.74% propylene glycol, 0.10% Poloxamer 188, 0.11% acetic acid and 0.09% sodium acetate;

0.50% D-Asn-Ile-Pro-Nva-Leu-Tyr-D-Ser-Phe-Ala-D-Ser-NH$_2$, 1.55% propylene glycol, 0.10% Poloxamer 188, 0.10% acetic acid and 0.24% sodium acetate;

1.00% D-Asn-Ile-Pro-Nva-Leu-Tyr-D-Ser-Phe-Ala-D-Ser-NH$_2$, 1.55% propylene glycol, 0.10% Poloxamer 188, 0.10% acetic acid and 0.24% sodium acetate;

1.00% D-Asn-Ile-Pro-Nva-Leu-Tyr-D-Ser-Phe-Ala-D-Ser-NH$_2$, 1.40% propylene glycol, 0.20% Poloxamer 188, 0.19% acetic acid and 0.30% sodium acetate;

1.00% D-Asn-Ile-Pro-Nva-Leu-Tyr-D-Ser-Phe-Ala-D-Ser-NH$_2$, 1.38% propylene glycol, 0.10% Tyloxapol, 0.19% acetic acid and 0.30% sodium acetate;

1.00% D-Asn-Ile-Pro-Nva-Leu-Tyr-D-Ser-Phe-Ala-D-Ser-NH$_2$, 1.25% propylene glycol, 0.10% Tyloxapol, 0.17% acetic acid and 0.41% sodium acetate;

1.00% D-Asn-Ile-Pro-Nva-Leu-Tyr-D-Ser-Phe-Ala-D-Ser-NH$_2$, 1.54% propylene glycol, 0.10% Tyloxapol, 0.19% acetic acid and 0.14% sodium acetate;

0.80% D-Asn-Ile-Pro-Nva-Leu-Tyr-D-Ser-Phe-Ala-D-Ser-NH$_2$, 1.54% propylene glycol, 0.10% Tyloxapol, 0.19% acetic acid and 0.14% sodium acetate;

0.50% D-Asn-Ile-Pro-Nva-Leu-Tyr-D-Ser-Phe-Ala-D-Ser-NH$_2$, 1.55% propylene glycol, 0.10% Tyloxapol, 0.19% acetic acid and 0.14% sodium acetate;

1.00% D-Asn-Ile-Pro-Nva-Leu-Tyr-D-Ser-Phe-Ala-D-Ser-NH$_2$, 1.53% propylene glycol, 0.10% Tyloxapol, 0.19% acetic acid and 0.14% sodium acetate;

1.00% D-Asn-Ile-Pro-Nva-Leu-Tyr-D-Ser-Phe-Ala-D-Ser-NH$_2$, 1.86% propylene glycol, 0.10% Tyloxapol, 0.13% acetic acid and 0.10% sodium acetate;

1.00% D-Asn-Ile-Pro-Nva-Leu-Tyr-D-Ser-Phe-Ala-D-Ser-NH$_2$, 1.67% propylene glycol, 0.10% Tyloxapol, 0.15% acetic acid and 0.11% sodium acetate; and 1.00% D-Asn-Ile-Pro-Nva-Leu-Tyr-D-Ser-Phe-Ala-D-Ser-NH$_2$, 1.62% propylene glycol, 0.10% Tyloxapol, 0.17% acetic acid and 0.13% sodium acetate.

6. The composition of claim 2, comprising, by weight: 1.00% D-Asn-Ile-Pro-Nva-Leu-Tyr-D-Ser-Phe-Ala-D-Ser-NH$_2$, 0.20% propylene glycol, 0.10% Tyloxapol, 0.07% acetic acid, 0.06% sodium acetate, 0.09% boric acid and 3.66% mannitol.

7. The composition of claim 2, comprising, by weight: 0.401% D-Asn-Ile-Pro-Nva-Leu-Tyr-D-Ser-Phe-Ala-D-Ser-NH$_2$, 0.193% propylene glycol, 0.097% Tyloxapol, 0.014% acetic acid, 0.138% sodium acetate, 0.09% boric acid and 3.65% mannitol.

8. The composition of claim 2, comprising, by weight: 0.4% D-Asn-Ile-Pro-Nva-Leu-Tyr-D-Ser-Phe-Ala-D-Ser-NH$_2$, 0.193% propylene glycol, 0.097% Tyloxapol, 0.015% acetic acid, 0.228% sodium acetate, 0.09% boric acid and 3.53% mannitol.

9. The composition of claim 2, comprising, by weight: 0.1% D-Asn-Ile-Pro-Nva-Leu-Tyr-D-Ser-Phe-Ala-D-Ser-NH$_2$, 0.193% propylene glycol, 0.097% Tyloxapol, 0.0065% acetic acid, 0.25% sodium acetate, 0.09% boric acid and 3.6% mannitol.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser-NH2

<400> SEQUENCE: 1

Xaa Ile Pro Xaa Leu Tyr Xaa Phe Ala Xaa
1               5                   10
```